US012644093B2

(12) United States Patent
Matsuura et al.

(10) Patent No.: US 12,644,093 B2
(45) Date of Patent: Jun. 2, 2026

(54) PYROTECHNIC CELL DISRUPTION APPARATUS AND PYROTECHNIC CELL DISRUPTION METHOD

(71) Applicant: Daicel Corporation, Osaka (JP)

(72) Inventors: David Matsuura, Solana Beach, CA (US); Adam Ariely, Encinitas, CA (US); Jacob Moebius, San Diego, CA (US)

(73) Assignee: Daicel Corporation, Osaka (JP)

( * ) Notice: Subject to any disclaimer, the term of this patent is extended or adjusted under 35 U.S.C. 154(b) by 1038 days.

(21) Appl. No.: 17/773,360

(22) PCT Filed: Oct. 28, 2020

(86) PCT No.: PCT/JP2020/040495

§ 371 (c)(1),
(2) Date: Apr. 29, 2022

(87) PCT Pub. No.: WO2021/085491

PCT Pub. Date: May 6, 2021

(65) Prior Publication Data

US 2024/0174971 A1 May 30, 2024

Related U.S. Application Data

(60) Provisional application No. 62/927,653, filed on Oct. 29, 2019, provisional application No. 62/927,661, (Continued)

(51) Int. Cl.
*C12M 1/00* (2006.01)
*C12M 1/42* (2006.01)

(52) U.S. Cl.
CPC ............ *C12M 47/06* (2013.01); *C12M 23/26* (2013.01); *C12M 35/04* (2013.01)

(58) Field of Classification Search
CPC ...... C12M 47/06; C12M 23/26; C12M 35/04; C12M 45/02; C12M 41/40; C12N 1/066
See application file for complete search history.

(56) References Cited

U.S. PATENT DOCUMENTS 3,458,139 A * 7/1969 Edebo ................. B02C 19/0056
                                                   241/1
8,840,835 B1 * 9/2014 Eidelman .................. A23L 5/32
                                                   422/20

(Continued)

FOREIGN PATENT DOCUMENTS

CN        1582173 A      2/2005
CN        108136129 A    6/2018
                    (Continued)

OTHER PUBLICATIONS

Miyazaki et. al, Development of Pyro-Drive Jet Injector With Controllable Jet Pressure, Journal of Pharmaceutical Sciences vol. 108, Issue 7, Jul. 2019, pp. 2415-2420 (Year: 2019).*

(Continued)

*Primary Examiner* — William H. Beisner
*Assistant Examiner* — Danielle B Henkel
(74) *Attorney, Agent, or Firm* — Morgan, Lewis & Bockius LLP

(57) ABSTRACT

This pyrotechnic cell disruption device is provided with: a pyrotechnic charge to be ignited which is configured to be burnt upon ignition; and a pressure chamber for housing a cell-containing fluid sample therein, said pressure chamber being configured to be pressurized when the pyrotechnic charge is ignited and burnt.

16 Claims, 20 Drawing Sheets

Related U.S. Application Data filed on Oct. 29, 2019, provisional application No. 62/927,659, filed on Oct. 29, 2019, provisional application No. 62/927,650, filed on Oct. 29, 2019, provisional application No. 62/927,658, filed on Oct. 29, 2019.

(56) References Cited

U.S. PATENT DOCUMENTS

| | | | |
|---|---|---|---|
| 9,475,027 B1* | 10/2016 | Eidelman | B01J 3/08 |
| 2002/0091311 A1* | 7/2002 | Eppstein | A61B 17/205 |
| | | | 604/20 |
| 2004/0124193 A1 | 7/2004 | Ritchie | |
| 2006/0064052 A1 | 3/2006 | Zhang et al. | |
| 2009/0105738 A1* | 4/2009 | Apperson | A61B 17/2202 |
| | | | 606/167 |
| 2012/0295356 A1 | 11/2012 | Jagadeesh | |
| 2018/0168789 A1* | 6/2018 | Shiku | A61K 9/0019 |
| 2021/0023302 A1 | 1/2021 | Miki et al. | |

FOREIGN PATENT DOCUMENTS

| | | | |
|---|---|---|---|
| EP | 0414044 A1 | 2/1991 | |
| JP | H03-076568 A | 4/1991 | |
| JP | H04-237486 A | 8/1992 | |
| JP | 2008-253245 A | 10/2008 | |
| JP | 2013-172677 A | 9/2013 | |
| JP | 2016-082879 A | 5/2016 | |
| WO | 2016/004539 A1 | 1/2016 | |
| WO | 2017/117666 A1 | 7/2017 | |
| WO | 2019049204 A1 | 3/2019 | |
| WO | 2019/156237 A1 | 8/2019 | |
| WO | 2019/157319 A1 | 8/2019 | |

OTHER PUBLICATIONS

International Search Report issued in corresponding International Patent Application No. PCT/JP2020/040495 dated Dec. 28, 2020.
International Preliminary Report on Patentability and Written Opinion issued in corresponding International Patent Application No. PCT/JP2020/040495 dated May 12, 2022.
Extended European Search Report issued in the corresponding Application No. 20883450.7, dated Nov. 8, 2023.
Office Action issued in the corresponding JP Application No. 2021-553662, dated Sep. 3, 2024.
Matsumoto, "Breakage of Micro organisms", Journal of the Society of Powder Technology, Feb. 17, 1988, vol. 25(5):27:33.

* cited by examiner

PYROTECHNIC CELL DISRUPTION APPARATUS AND PYROTECHNIC CELL DISRUPTION METHOD

TECHNICAL FIELD

The present invention relates to a pyrotechnic cell disruption apparatus and a pyrotechnic cell disruption method.

BACKGROUND ART

Cell lysis, also known as cellular disruption, is used for breaking down the outer boundary or cell membrane in order to release inner cellular materials such as DNA, RNA, protein or organelles from a cell. Such release of intracellular materials is important for various types of molecular diagnostics. To name a few, such diagnostics may encompass pathogen detection platforms, immunoassays for point of care diagnostics, protein purification for studying protein function and structure, cancer diagnostics, drug screening, mRNA transcriptome determination, and analysis of the composition of specific proteins, lipids, and nucleic acids individually or as complexes.

Patent documents 1 and 2 and the like disclose point of care devices for detecting a nucleic acid. The point of care devices disclosed in Patent documents 1 and 2 and the like are adapted to receive samples, include extraction chambers that include lysis for extracting and dissolving samples and heaters, and cause a nucleic acid to be released by dissolving the samples in the extraction chambers.

CITATION LIST

Patent Document

Patent Document 1: International Publication No. WO 2016/004539
Patent document 2: International Publication No. WO 2017/117666

SUMMARY OF INVENTION

Technical Problem

Small sample sizes, specifically when taken from a human or animal, have a number of advantages. Apart from allowing less invasive sampling methods, also the risk of contaminating the environment is reduced. Small sample sizes also allow for a higher degree of automation. Further, samples are easier to transport into the device, as well as to safely discard these after testing is completed with a lower risk of both contaminating the sample prior to testing, as well as a lower risk of contaminating the environment. In addition, small sample sizes are favorable for complying with various regulatory standards to clinical laboratory testing. Due to lower risks being involved with small sample sizes, handling these samples may also allow to some degree lesser trained technicians. Small sample sizes work also well for single use disposable, point of care devices (POC) where size and unit cost are critical.

Other types of samples may be plants and fungi as well. For instance, a farmer may want to know what pathogen or bio-engineered agent is affecting a crop. Food safety and inspections are other fields where small sample sized may be desirable.

Microfluidic technology involves the handling and manipulation of very small volumes of fluids such as microliters or smaller and offers various advantages, which include low reagent volume, high surface to volume ratio, low cost, and easy handling of small volumes of fluids that are suited for cell analysis. Microfluidic devices have been proposed for cell lysis. However, various challenges come with cellular disruption in very small fluid volumes, one of which being how to build up pressure. Also, some cell disruption methods may require building up and releasing pressure over certain short time spans for optimizing efficiency. However, in a case in which cell disruption is performed by hydraulic press, it takes a time to build up pressure, and a large-scaled device may be required.

Another factor is heat. While excessive heat over a longer time period may not be desirable because of its potential to damage proteins that are desirable to be extracted from the interior of the cell, a short-term exposure to heat in combination with pressure may have an additional positive effect on the cell disruption.

Cell destruction by heat lysis requires significant power. Chemical lysis uses strong alkaline materials such as KOH. Chemical lysine reagents may require an additional step of buffering/neutralization before the lysed sample is suitable for the downstream assay.

Solution to Problem

According to one aspect of the invention, a pyrotechnic cell disruption apparatus includes: a pyrotechnic charge configured to be ignited and to combust upon ignition; and a pressure chamber including an interior space that is configured to receive a fluid sample containing cells and to be pressurized upon ignition and combustion of the pyrotechnic charge.

Advantageous Effects of Invention

According to the technique of the present disclosure, it is possible to provide a technique capable of improving disruption of cells contained in a fluid sample as compared with the related art.

DESCRIPTION OF EMBODIMENTS

Figure 1:
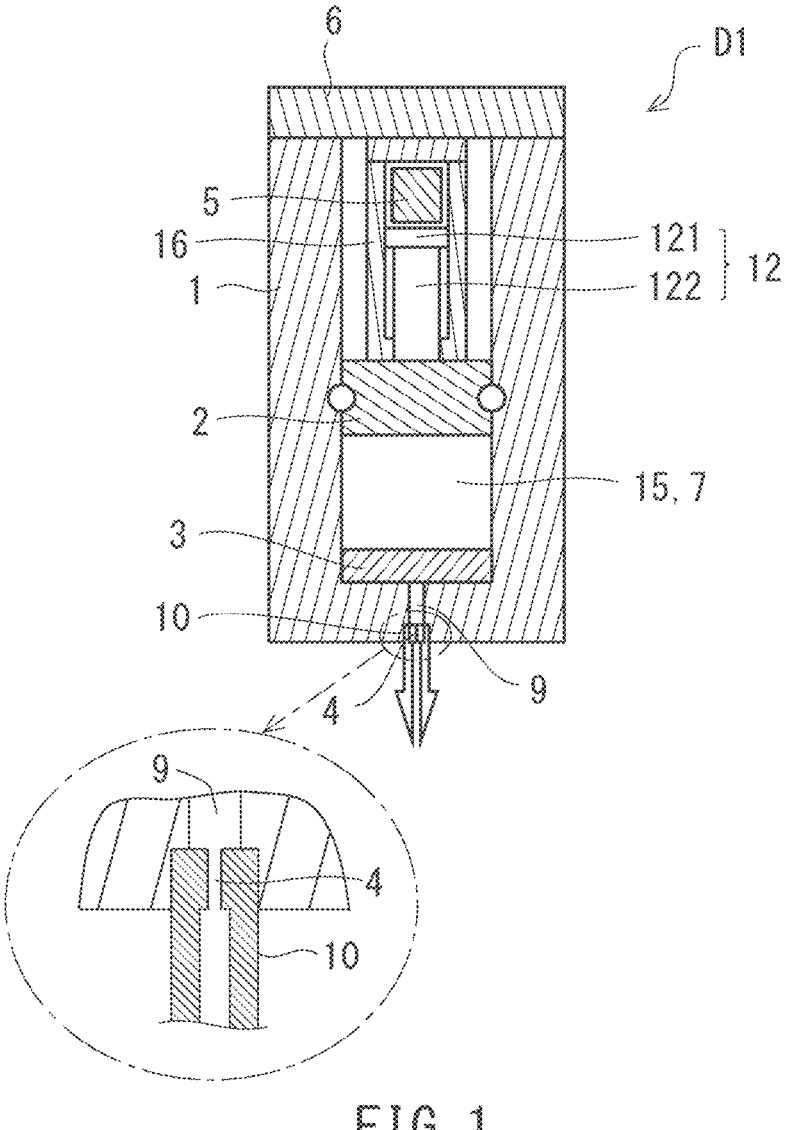
FIG. 1 illustrates a schematic sectional view of a first pyrotechnic cell disruption apparatus in a first configuration prior to pressurizing.

A pyrotechnic cell disruption apparatus disclosed in each embodiment described below includes: a pyrotechnic charge (explosive) configured to be ignited and to combust upon the ignition; and a pressure chamber configured to receive a fluid sample containing cells and to be pressurized upon the ignition and the combustion of the pyrotechnic charge. Also, a pyrotechnic cell disruption method disclosed in each embodiment includes: receiving a fluid sample containing cells in a pressure chamber configured to be compressed by a pyrotechnic charge; and pressurizing a fluid sample received in the pressure chamber by igniting and combusting the pyrotechnic charge.

It is possible to realize cell disruption in a very short time by mainly using a fuel gas of the pyrotechnic charge as a pressurization source for pressurizing the fluid sample in this manner. It is thus possible to realize cell disruption in a very short time as compared with a case in which the fluid sample is compressed by hydraulic press. Also, the cells are not exposed to excessive heat for a long period of time as in heat lysis, and it is thus possible to curb damage on the cells. Additionally, it is possible to achieve cell disruption without using any chemical substances that are not easily handled, unlike chemical lysis using chemical substances.

Also, the pyrotechnic cell disruption apparatus according to the present disclosure can include an initiator (igniter) including a housing that receives the pyrotechnic charge. As the initiator, an initiator for causing a vehicle airbag to operate, for example, can be suitably used, and ignition control of the pyrotechnic charge is performed by receiving operation power supply from an external power source. Although the pyrotechnic charge is not particularly limited, examples thereof include ZPP (zirconium-potassium perchlorate), ZWPP (zirconium-tungsten-potassium perchlorate), THPP (titanium hydride-potassium perchlorate), and lead tricinate.

Although the fluid sample received in the pressure chamber according to the present disclosure is not particularly limited as long as the fluid sample is a sample of a fluid containing cells, examples thereof include a cell suspension in which cells are dispersed in a liquid. The cells contained in the fluid sample are not particularly limited, and may be cells collected from humans or animals, or may be plant cells, fungi, or other cells.

In the present disclosure, although the amount (the scale or the size) of the fluid sample to be received in the pressure chamber is not particularly limited, it is possible to employ a very small amount of microliter ($\mu$L) order, for example. For example, the amount of the fluid sample may be 10 $\mu$L or more and 500 $\mu$L or less. Alternatively, any of 20 $\mu$L, 50 $\mu$L, 100 $\mu$L, 150 $\mu$L, 200 $\mu$L, and 300 $\mu$L, for example, may be employed as an upper limit value or a lower limit value of the amount of the fluid sample. It is a matter of course that a larger scale of milliliter (mL) order or more can be used for the amount of the fluid sample.

Also, the number of cells contained in the fluid sample is also not particularly limited. For example, the number of cells contained in the fluid sample may be $1\times10^2$ cells/cm$^3$ or more and $1\times10^9$ cells/cm$^3$ or less. Alternatively, any of $1\times10^3$ cells/cm$^3$, $1\times10^4$ cells/cm$^3$, $1\times10^5$ cells/cm$^3$, $1\times10^6$ cells/cm$^3$, $1\times10^7$ cells/cm$^3$, and $1\times10^8$ cells/cm$^3$, for example, may be used as an upper limit value or a lower limit value of the number of cells contained in the fluid sample.

According to the pyrotechnic cell disruption apparatus and the pyrotechnic cell disruption method according to the present disclosure, it is possible to significantly shorten a time required to ignite and combust the pyrotechnic charge to pressure the fluid sample containing cells received in the pressure chamber and thereby to disrupt the cells and to extremely shorten a time during which the cells contained in the fluid sample are exposed to heat during the pressurization. Although the time during which the cells are exposed to heat during the pressurization of the fluid sample is not particularly limited in the pyrotechnic cell disruption apparatus and the pyrotechnic cell disruption method according to the present disclosure, the time may be 0.1 ms (milliseconds) or more and 500 ms or less, for example. Alternatively, any of 1 ms, 10 ms, 20 ms, 30 ms, 40 ms, 50 ms, 60 ms, 70 ms, 80 ms, 90 ms, 100 ms, 200 ms, 300 ms, and 400 ms may be employed as an upper limit value or a lower limit value of the time during which the fluid sample is exposed to heat during the pressurization. Although the time (disruption processing duration) until disruption processing of the cells contained in the fluid sample is completed after operations of the pyrotechnic cell disruption apparatus according to the present disclosure is started is not particularly limited, the time may be 0.1 ms or more and 1 s (second) or less. Alternatively, any of 1 ms, 10 ms, 100 ms, and 500 ms, for example, may be employed as an upper limit value or a lower limit value of the disruption processing duration.

The pressure chamber in the pyrotechnic cell disruption apparatus according to the present disclosure can receive an arbitrary material that is different from the fluid sample in addition to the fluid sample. Examples of the material other than the fluid sample to be received in the pressure chamber include water, other arbitrary liquid, or other materials such as a water-absorbent polymer, and the pressure chamber may be filled with these. In this manner, it is possible to smooth a pressure shock wave when the pressure chamber is pressurized by igniting and combusting the pyrotechnic charge.

The pyrotechnic cell disruption apparatus according to the present disclosure can include an orifice that distributes the fluid sample after the fluid sample received in the pressure chamber is pressurized with combustion gas of the pyrotechnic charge. The orifice is a minute pathway through which the fluid sample pressurized in the pressure chamber is distributed.

The orifice may be a precision orifice that has an orifice diameter, for example, and is formed as a channel with a flow path length that is several times as long as the orifice diameter. The diameter of the orifice can be set to a dimension that allows distribution of the fluid sample and enables sufficient shear stress to act on the fluid sample upon the distribution. Although the diameter of the orifice can be set to a different dimension in accordance with the size, the number, the type, and the like of the cells contained in the fluid sample, the diameter may be 1 μm or more and 500 μm or less, for example. Alternatively, any of 10 μm, 20 μm, 30 μm, 40 μm, 50 μm, 60 μm, 70 μm, 80 μm, 90 μm, 100 μm, 200 μm, 300 μm, and 400 μm, for example, may be employed as an upper limit value or a lower limit value of the diameter of the orifice.

The pyrotechnic cell disruption apparatus according to the present disclosure can include a pressure relief that pressurizes the fluid sample received in the pressure chamber with combustion gas of the pyrotechnic charge and then releases a pressure from the pressure chamber. The pressure relief can include a pressure release valve, a rupture plate, and the like that opens the pressure camber to an exterior space. Although a pressure value at which the pressure release valve is opened or a pressure value at which the rupture plate ruptures is not particularly limited, a pressure value of 20,000 psi or more and 50,000 psi or less may be set, for example. Alternatively, any of 25,000 psi, 30,000 psi, 35,000 psi, 40,000 psi, and 45,000 psi, for example, may be employed as an upper limit value or a lower limit value of the pressure value at which the pressure release valve is opened or the pressure value at which the rupture plate ruptures.

Embodiments according to the present disclosure will be described below with reference to the drawings. Note that each of the configurations, combinations thereof, and the like in each embodiment is an example, and additions, omissions, substitutions, and other changes of the configuration may be made as appropriate without departing from the spirit of the present invention. The present disclosure is not limited by the embodiments and is limited only by the claims.

First Embodiment

FIG. 1 illustrates a schematic sectional view of a first pyrotechnic cell disruption apparatus in a first configuration prior to pressurizing. This first pyrotechnic cell disruption apparatus includes a cylinder body 1 with a piston 2 pressing a fluid sample 3 through an orifice 4 and releasing (discharging) the sample to atmospheric pressure. The orifice is formed in a separate part 10 that is bonded or pressed into the pressure chamber outlet such as a release channel 9. The pressure source is not hydraulic, but comes from igniting a pyrotechnic charge 5. The pyrotechnic charge disruption apparatus further comprises a cap 6, allowing to open and close the apparatus, for instance for filling the apparatus with the fluid sample 3 or for including the pyrotechnic charge 5.

Figure 2:
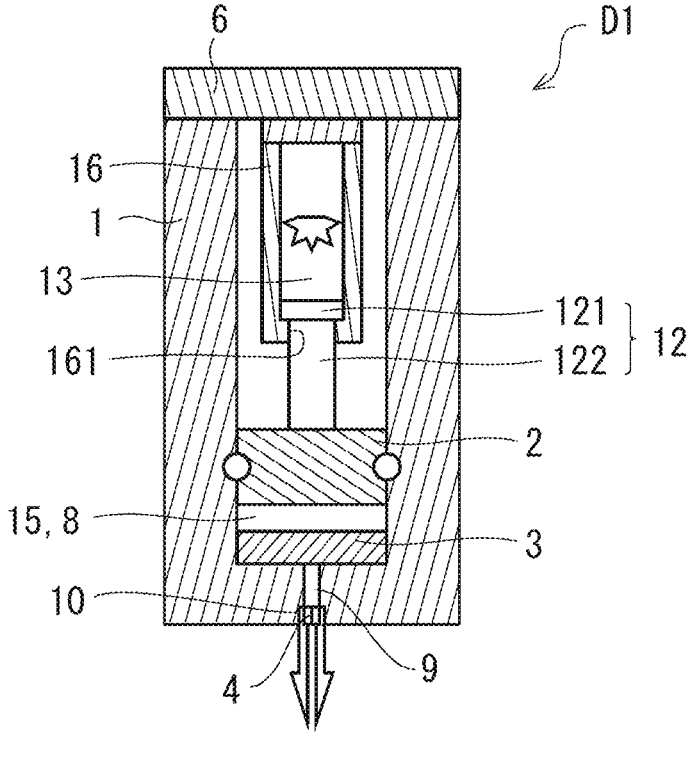
FIG. 2 illustrates a schematic sectional view of the first pyrotechnic cell disruption apparatus in a second configuration after pressurizing.

In the first configuration illustrating the apparatus prior to pressurizing, a low-pressure space 7 of the pressure chamber 15 may be provided between the piston 2 and the fluid sample 3. After igniting the pyrotechnic charge 5, the apparatus assumes a second configuration as illustrated in FIG. 2, where the low-pressure space 7 as illustrated in the configuration according to FIG. 1 has turned into a high-pressure space 8 of smaller volume but under higher pressure. In the alternative, it would also be possible to provide no space between the piston and the sample. Also, the low-pressure space 7 could be filled with a variety of different materials, such as liquids, but also other materials such as water absorbent polymer, the latter smoothening the pressure shock wave to some extent as that may be helpful to achieve the desired cell disruption results. The sample could be filled in after removing the cap and the piston, but it would also be possible to include the sample through the release channel 9, specifically after removing an insert including the precision orifice 4.

The precision orifice 4 generates shear stress as the cells move through it. The cells then experience rapid decompression once they have passed through the precision orifice 4. Sample sizes could for instance be as small as 150 μL or smaller such as for instance 10 μL. Also, bigger sample sizes such as one milliliter might be possible. Given that the sample size is typically very small, the release (discharge) time through the precision orifice 4 is very short. Including gas in the low-pressure space 7 that is quickly compressed after ignition of the pyrotechnic charge 5, this gas is heated in a very short time by compression, and is exposed to that heat for only a short time prior to its release (discharge) through the precision orifice 4. This time is short enough to prevent damage of the cell material, but long enough for helping with the cellular disruption process.

The pyrotechnic charge is accommodated in a separate pyrotechnic charge chamber housing 16 that also includes a first piston 12. Such pyrotechnic charge chamber housing 16 may include a first cylinder chamber 13 accommodating the pyrotechnic charge 5 and the first piston 12. The first piston 12 is movable relative to the first cylinder chamber 13 under a pressure generated by igniting and combusting the pyrotechnic charge 5. The first piston 12 is connected to a second piston, here at the aforementioned piston 2 that is provided in said pressure chamber 15 so that the piston 2 forms one wall of the pressure chamber 15. The first cylinder chamber 13 is provided within the pyrotechnic charge chamber housing 16 that is at least in part accommodated within the pressure chamber 15.

As described above, a first pyrotechnic cell disruption apparatus D1 (see FIGS. 1 and 2) according to a first embodiment includes: a pyrotechnic charge 5 configured to be ignited and to combust upon the ignition; a pressure chamber 15 (low-pressure space 7/high-pressure space 8) configured to receive a fluid sample 3 and to be pressurized upon the ignition and the combustion of the pyrotechnic charge 5; and a release channel 9 that connects the pressure chamber 15 (low-pressure space 7/high-pressure space 8) to an exterior space. The release channel 9 includes a precision orifice 4 configured as a pathway of the fluid sample 3. The first pyrotechnic cell disruption apparatus D1 includes a cylinder body 1 including the pressure chamber 15 therein. The cylinder body 1 has a bottomed tubular shape with an upper portion formed as an open end as illustrated in FIGS. 1 and 2, for example, and a cap 6 can be freely attached to and detached from the open end. The cylinder body 1 may be a housing member with a bottomed tubular shape. Also, the pyrotechnic charge chamber housing 16 is integrally fixed to an inner surface side of the cap 6, for example. In the example illustrated in FIGS. 1 and 2, the fluid sample 3 is received in the pressure chamber 15 by the fluid sample 3 being placed on the bottom of the cylinder body 1.

Once the first pyrotechnic cell disruption apparatus D1 operates, ignition control of the pyrotechnic charge 5 is performed, and the pyrotechnic charge 5 combusts, for example. Here, the first pyrotechnic cell disruption apparatus D1 may include an initiator (igniter) for performing the ignition control of the pyrotechnic charge 5, and the pyrotechnic charge 5 and a housing holding this may configure a part of the initiator. The initiator further includes a wire connected to an external power source, for example, and can perform the ignition control of the pyrotechnic charge 5 by receiving operation power supply from the external power source.

As described above, in the first pyrotechnic cell disruption apparatus D1, the pyrotechnic charge 5 and the first piston 12 are received in the first cylinder chamber 13 formed in the pyrotechnic charge chamber housing 16 that has at least a part stored in the cylinder body 1. Therefore, the pyrotechnic charge chamber housing 16 can also be referred to as a "first cylinder chamber housing" that forms the first cylinder chamber 13. As illustrated in FIG. 1, in a first configuration (before pressurizing) of the first pyrotechnic cell disruption apparatus D1, the pyrotechnic charge 5 is received in an upper region of the first cylinder chamber 13, and at least a part of the first piston 12 is received in a lower region thereof. As illustrated in FIG. 1, the pyrotechnic charge 5 is received in the first cylinder chamber 13 fixed by the pyrotechnic charge chamber housing 16 disposed to be separated from the cylinder body 1 of the pressure chamber 15 before the first pyrotechnic cell disruption apparatus D1 operates. Here, the first cylinder chamber 13 can be specified as a "pyrotechnic charge chamber" that receives the pyrotechnic charge 5.

Here, the first piston 12 includes a head unit 121 and a rod unit 122 that extends downward from the head unit 121 and is integrated with the head unit 121. Also, a rod insertion hole 161 is formed in a penetrating manner at the bottom of the pyrotechnic charge chamber housing 16. In a state in which the rod unit 122 of the first piston 12 is inserted into the rod insertion hole 161, a lower end of the rod unit 122 is connected to the piston 2 (second piston) received in the pressure chamber 15 (outside the first cylinder chamber 13).

The first piston 12 is configured to be movable in the up-down direction of the first cylinder chamber 13, for example, in a state in which the head unit 121 is received in the pyrotechnic charge chamber housing 16. Also, the diameter of the head unit 121 of the first piston 12 may be larger than the diameter of the rod insertion hole 161, such that the head unit 121 is configured not to fall out of the first cylinder chamber 13.

A region sandwiched between the bottom cylinder body 1 and the piston 2 (second piston) in the pressure chamber 15 will also be referred to as a "second cylinder chamber". The second cylinder in the pressure chamber 15 forms a low-pressure space 7 (see FIG. 1) in the first configuration of the first pyrotechnic cell disruption apparatus D1 before pressurizing (before operations), and forms a high-pressure space 8 (see FIG. 2) in the second configuration (see FIG. 2) after the pressurizing (after operations).

Once the ignition control of the pyrotechnic charge 5 is performed by the initiator, for example, when the first pyrotechnic cell disruption apparatus D1 operates, combustion gas is generated by combustion of the pyrotechnic charge 5, and as a result, the pressure inside the first cylinder chamber 13 increases. As a result, the head unit 121 of the first piston 12 is pressed under the pressure generated by the combustion of the pyrotechnic charge 5, and the first piston 12 moves downward relative to the first cylinder chamber 13. With this, the piston 2 (second piston) connected to the rod unit 122 of the first piston 12 also moves downward (the side of the bottom of the cylinder body 1) in conjunction therewith. In this manner, the volume of the second cylinder chamber in the pressure chamber 15 decreases, and the second cylinder chamber changes from the low-pressure space 7 at a low pressure to the high-pressure space 8 at a high pressure. As a result, the fluid sample 3 received in the second cylinder chamber (here, the high-pressure space 8) in the pressure chamber 15 is pressurized, and it is thus possible to disrupt the cells (for example, extracellular shells (cellular membranes, cellular walls, and the like)) included in the fluid sample 3. Note that "the low-pressure space 7/the high-pressure space 8" described together in the present specification indicates the same space inside the pressure chamber 15. In other words, this means that the space is formed as the low-pressure space 7 at a low pressure before operations (before pressurizing) of the pyrotechnic cell disruption apparatus D1 and the low-pressure space 7 changes to the high-pressure space 8 at a high pressure after operations (after pressurizing) of the apparatus, and the same applies to the following embodiments.

Also, the fluid sample 3 received in the pressure chamber 15 (high-pressure space 8) pressurized by the piston 2 (second piston) as described above is pushed into a release channel 9 that communicates with the high-pressure space 8 and is then discharged to the outside of the apparatus through the release channel 9. The fluid sample 3 that has passed through the release channel 9 is collected by a collecting container, which is not illustrated, under an atmospheric pressure, for example. Since the diameter of the precision orifice 4 is very small, the precision orifice generates shear stress when the fluid sample 3 passes through the precision orifice 4, and causes the shear stress to act on the fluid sample 3. In the present embodiment, it is possible to suitably disrupt the cells by applying the shear stress generated during passing through the precision orifice 4 to the cells contained in the fluid sample 3. Moreover, the fluid sample 3 that has passed through the precision orifice 4 is suddenly decompressed by being exposed to the atmospheric pressure. As a result, the fluid sample 3 suddenly expands, and the disruption of the cells contained in the fluid sample 3 can thus be promoted by the expansion pressure. As described above, according to the first pyrotechnic cell disruption apparatus D1, it is possible to perform various kinds of cell analysis, cell diagnosis, and the like by disrupting the cells contained in the fluid sample 3 and separating intracellular substances such as DNA, RNAs, proteins, or organelles from the cells, for example.

Also, according to the first pyrotechnic cell disruption apparatus D1, it is possible to obtain the disrupted cells by employing ignition and combustion of the pyrotechnic charge 5, rather than the hydraulic scheme, as a pressure source for pressurizing the fluid sample 3. By causing the pistons (the first piston 12 and the second piston) to operate by the combustion gas generated by catching fire of the pyrotechnic charge 5 in this manner, it is possible to instantaneously form the high-pressure space 8 inside the pressure chamber 15, to quickly pressurize the fluid sample 3, and to discharge the fluid sample 3 to the outside through the precision orifice 4. It is thus possible to realize efficient cell disruption in a short time. Moreover, according to the first pyrotechnic cell disruption apparatus D1, it is possible to pressurize the fluid sample 3 in a short time as described above and thereby to curb exposure of the cells contained in the fluid sample 3 to a high temperature over a long time. It is thus possible to suitably curb damage on the cells contained in the fluid sample 3.

Moreover, according to the first pyrotechnic cell disruption apparatus D1, the pyrotechnic charge 5 is used as a pressure source for pressurizing the fluid sample 3, and it is thus possible to realize efficient cell disruption with a small amount of pressure source. As a result, it is possible to realize a compact pyrotechnic cell disruption apparatus. Furthermore, it is possible to state that the pyrotechnic charge 5 used as the pressure source for pressurizing the fluid sample 3 is a material suitable for precise control of the pressure (output) to be generated. Therefore, it is possible to precisely perform pressure control when the cells contained in the fluid sample 3 is pressurized even if the size of the fluid sample 3 received in the pressure chamber 15 is in microliter order. In this manner, it is possible to realize a decrease in sample size, which has not been able to be realized by cell disruption apparatuses in the related art (French Press (registered trademark), for example). As described above, according to the present embodiment, the size of the fluid sample 3 can be a very small size, and it is thus possible to perform less invasive collection of cells in a case in which the cells are collected from humans or animals, in particular. Also, it is possible to reduce the sample size, thereby to reduce the risk of contaminating the environment, and to achieve more advanced automation. Furthermore, the handling becomes easier even for persons who are not skilled, by reducing the sample size. Also, the small sample size satisfactorily functions for disposable point of care devices (POCs), for which sizes and unit cost are important, it is possible to provide a pyrotechnic cell disruption apparatus suitable for the point of care.

Second Embodiment

Figure 3:
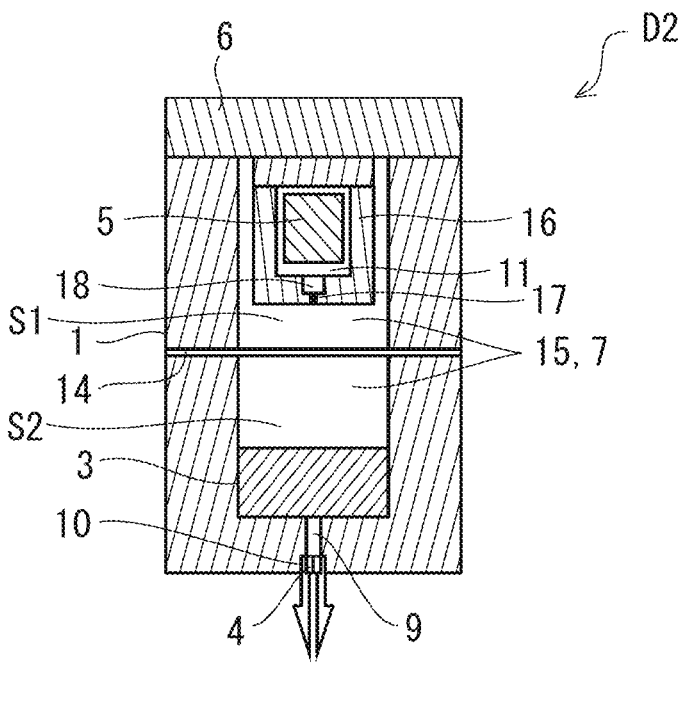
FIG. 3 illustrates a schematic sectional view of a second pyrotechnic cell disruption apparatus in a first configuration prior to pressurizing.
Figure 4:
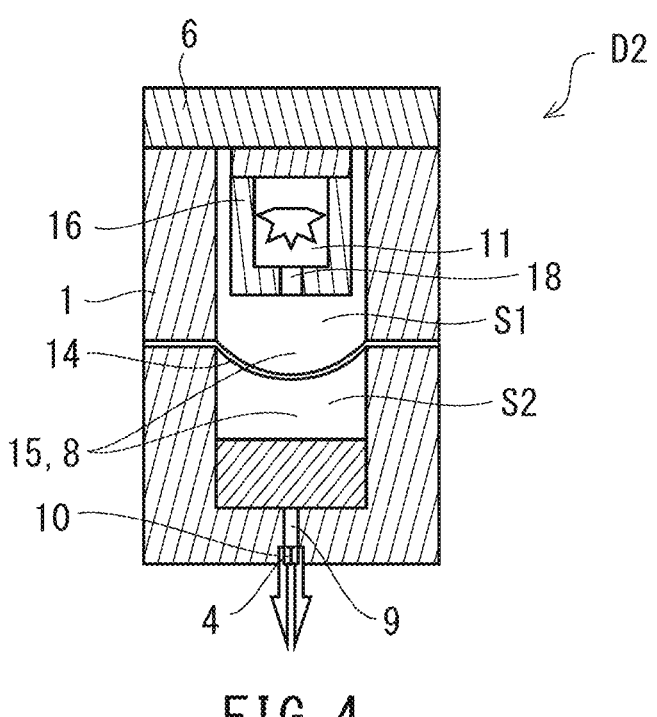
FIG. 4 illustrates a schematic sectional view of the second pyrotechnic cell disruption apparatus in a second configuration after pressurizing.

FIG. 3 illustrates a schematic sectional view of a second pyrotechnic cell disruption apparatus in a first configuration prior to pressurizing and FIG. 4 illustrates a schematic sectional view of the second pyrotechnic cell disruption apparatus in a second configuration after pressurizing. The embodiment illustrated in FIGS. 3 and 4 is essentially a variation of the embodiment illustrated in FIGS. 1 and 2.

Similar elements are denoted by the same reference numerals. The embodiment according to FIGS. 3 and 4 does not comprise a piston, but in lieu of that piston a deformable diaphragm 14 dividing the low-pressure space 7 and accordingly the high pressures space 8 into two parts. Consequently, the pressure chamber 15 is at least in part defined by the deformable diaphragm 14 that is configured to be deformed under a pressure generated by the pyrotechnic charge 5 upon ignition and combustion of the pyrotechnic charge 5, as illustrated in FIG. 4, reducing a volume of the pressure chamber upon deformation and consequently pressurizing the pressure chamber upon deformation.

The charge chamber housing 16 includes a predetermined breaking point 17 at the bottom of a pyrotechnic charge pressure release channel 18. The fluid sample 3 can be inserted in the apparatus according to FIGS. 3 and 4 by either dividing the housing at the diaphragm position into two parts, removing the diaphragm, and assembling the housing holding the diaphragm in place.

An advantage of the embodiment illustrated in FIGS. 3 and 4 is prevention of mixing the byproducts of the pyrotechnic charge after ignition with the fluid sample 3 as the diaphragm 14 hermetically seals off the fluid sample 3 from the pyrotechnic charge 5. The diaphragm preferably is made from metal, but also other materials would be possible, for instance polymers such as PE, PP or other plastically deformable polymers. Other options are composite structures like coated fabrics or polymer coated glass holding glass at together by the polymer coating even when glass fractures. Also, a bellows like structure may be beneficial as a diaphragm. Further options are using a mesh screen that would serve to catch particulate and protect the sample from debris but not be a pressure barrier—which would essentially be a hybrid between the embodiments illustrated in FIG. 3 and FIG. 5.

As described above, in a second pyrotechnic cell disruption apparatus D2 (see FIGS. 3 and 4) according to a second embodiment, the pyrotechnic charge 5 is received in a different pyrotechnic charge chamber 11 that is separated from the pressure chamber 15 formed inside the cylinder body 1. The pyrotechnic charge chamber 11 is formed inside the pyrotechnic charge chamber housing 16, and as illustrated in FIG. 3, the bottom of the pyrotechnic charge chamber housing 16 is provided with the pressure release channel 18. The pressure release channel 18 is a channel 18 for releasing a pressure generated inside the pyrotechnic charge chamber housing 16 upon ignition and combustion of the pyrotechnic charge 5 to the pressure chamber 15 where the diaphragm 14 is disposed. In the second pyrotechnic cell disruption apparatus D2, the pressure chamber 15 is sectioned into two spaces by the diaphragm 14. In the pressure chamber 15 sectioned by the diaphragm 14, the space on the side of the pyrotechnic charge chamber housing 16 will be referred to as a "first interior space S1" while the space on the side of the bottom of the cylinder body 1 on which the fluid sample 3 is placed will be referred to as a "second interior space S2". Note that the first interior space S1 of the pressure chamber 15 does not include an interior space of the pyrotechnic charge chamber housing 16. As illustrated in FIGS. 3 and 4, the fluid sample 3 is received in the second interior space S2 of the pressure chamber 15. Also, the release channel 9 including the precision orifice 4 is connected to the second interior space S2 of the pressure chamber 15, such that the second interior space S2 and the exterior space can communicate via the release channel 9 including the precision orifice 4.

In the second pyrotechnic cell disruption apparatus D2, the pressure release channel 18 of the pyrotechnic charge chamber housing 16 does not communicate with the first interior space S1 of the pressure chamber 15 in a state before operations (before pressurizing) (the first configuration illustrated in FIG. 3) and is blocked by a breaking point 17 formed at the bottom of the pyrotechnic charge chamber housing 16 facing the first interior space S1 (pressure chamber 15). Note that the pressure release channel 18 may be formed as a recess formed at the bottom of the pyrotechnic charge chamber housing 16, for example, and the breaking point 17 may be formed by a portion with a thickness reduced by forming the pressure release channel 18. In this case, the breaking point 17 in the pyrotechnic charge chamber housing 16 is formed as a vulnerable portion that is more vulnerable than the other portions. The breaking point 17 in the pyrotechnic charge chamber housing 16 is disposed to face the first interior space S1.

Once the pyrotechnic charge 5 is ignited and combusted when the second pyrotechnic cell disruption apparatus D2 is operating, the pressure in the pyrotechnic charge chamber 11 increases due to combustion gas generated by the pyrotechnic charge 5, and the breaking point 17 ruptures. As a result, the pyrotechnic charge chamber 11 and the first interior space S1 of the pressure chamber 15 communicate via the pressure release channel 18, and the combustion gas of the pyrotechnic charge 5 is introduced into the first interior space S1. In this manner, the diaphragm 14 is deformed from the side of the first interior space S1 toward the side of the second interior space S2 as illustrated in FIG. 4, and the volume of the first interior space S1 increases while the volume of the second interior space S2 decreases as compared with the state illustrated in FIG. 3. As a result, the pressure in the second interior space S2 in which the fluid sample 3 is received increases, and the second interior space S2 changes from the low-pressure space 7 to the high-pressure space 8. Note that although the volume of the first interior space S1 increases as compared with the state illustrated in FIG. 3, the combustion gas of the pyrotechnic charge 5 flows in through the pressure release channel 18, and the first interior space S1 thus also changes from the low-pressure space 7 to the high-pressure space 8 in accordance with the operations of the second pyrotechnic cell disruption apparatus D2. Note that in the present embodiment, the cap 6 is detachably provided at the upper end opening of the cylinder body 1 similarly to the first embodiment, and it is possible to fix the pyrotechnic charge chamber housing 16 that receives the pyrotechnic charge 5 to the inside of the cap 6.

As described above, the fluid sample 3 received in the second interior space S2 of the pressure chamber 15 is pressurized by the second pyrotechnic cell disruption apparatus D2 operating. As a result, it is possible to disrupt the cells contained in the fluid sample 3. Since the release channel 9 including the precision orifice 4 is connected to the second interior space S2 of the pressure chamber 15 as described above, the pressurized fluid sample 3 is pushed into the release channel 9. Then, disruption of the cells contained in the fluid sample 3 is promoted by shear stress generated when the fluid sample 3 passes through the precision orifice 4 being applied to the fluid sample 3. Also, the cell disruption is further promoted by the fluid sample 3 being exposed to the atmospheric pressure after passing through the precision orifice 4, discharged out of the apparatus and being thus suddenly decompressed and expanded. The fluid sample 3 on which the cell disruption processing has been performed in this manner can be collected in a collecting container similarly to the first embodiment. According to the second pyrotechnic cell disruption apparatus D2 in the present embodiment, effects similar to those of the first pyrotechnic cell disruption apparatus D1 are obtained. Note that in a case in which the diaphragm 14 is formed by a metal material, aluminum, cast iron, or stainless steel, for example, may be used as the material.

Third Embodiment

Figure 5:
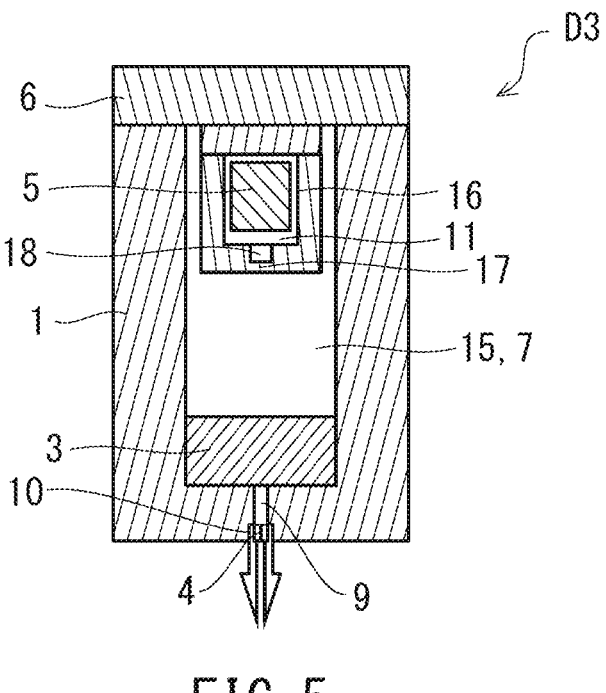
FIG. 5 illustrates a schematic sectional view of a third pyrotechnic cell disruption apparatus in a first configuration prior to pressurizing.
Figure 6:
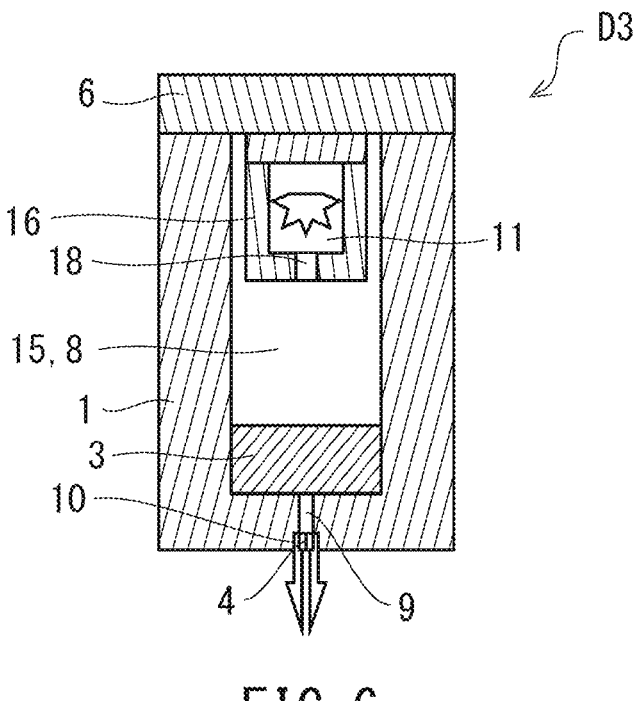
FIG. 6 illustrates a schematic sectional view of the third pyrotechnic cell disruption apparatus in a second configuration after pressurizing.

FIG. 5 illustrates a schematic sectional view of a third pyrotechnic cell disruption apparatus in a first configuration prior to pressurizing and FIG. 6 illustrates a schematic sectional view of the third pyrotechnic cell disruption apparatus in a second configuration after pressurizing. This third embodiment is very similar to the second embodiment, except for omitting the diaphragm 14 entirely. Therefore, the separate pyrotechnic charge chamber housing 16 opens directly into the pressure chamber upon ignition and combustion of the pyrotechnic charge. This embodiment simplifies loading of the sample into the apparatus and minimizes seals and moving parts but exposes the sample by the byproducts of the pyrotechnic charge after its ignition. This may however be acceptable depending on the particular sample and the desired inner cell molecules of interest if these do not chemically interact with said byproducts or gets otherwise contaminated to an extent that a proper detection/diagnostics is compromised. Chemical interaction with the byproducts of the pyrotechnic charge could also be used to an advantage if the pyro byproducts enable/enhance lysing. Certain chemicals and detergents are used by themselves to lyse cells. Further, the heat generated by the pyrotechnic charge may also be an advantage in enabling/enhancing lysing. Mechanical lysing could also be utilized in this device by adding hard beads or other projectiles/agitators to the reaction chamber. Like in the embodiments of FIGS. 1-4, similar reference numerals are used for similar elements in this third embodiment compared to the first and second embodiments.

In a third pyrotechnic cell disruption apparatus D3 (see FIGS. 5 and 6) configured as described above, the pressure chamber 15 is not sectioned by a diaphragm or the like. The pressure chamber 15 is formed as a low-pressure space 7 before operations (before pressurizing) of the third pyrotechnic cell disruption apparatus D3. Also, the pressure chamber 15 changes from the low-pressure space 7 to the high-pressure space 8 by the inner pressure of the pressure chamber 15 rising after operations (after pressurizing) of the third pyrotechnic cell disruption apparatus D3. As is obvious from FIG. 5, the structure of the pyrotechnic charge chamber housing 16 that receives the pyrotechnic charge 5 before operations (before pressurizing) of the third pyrotechnic cell disruption apparatus D3 is similar to that of the second pyrotechnic cell disruption apparatus D2, and the pyrotechnic charge chamber housing 16 is provided with the pressure release channel 18 and the breaking point 17. The pressure release channel 18 does not communicate with the interior space (low-pressure space 7) of the pressure chamber 15 before operations (before pressurizing) of the third pyrotechnic cell disruption apparatus D3. Then, the pyrotechnic charge 5 is ignited with operations of the apparatus, and the vulnerable breaking point 17 ruptures under a pressure caused by combustion gas generated by combustion of the pyrotechnic charge 5. In this manner, the pyrotechnic charge chamber housing 16 (pyrotechnic charge chamber 11) opens directly to the pressure chamber 15 (low-pressure space 7), and the pressure in the pyrotechnic charge chamber housing 16 is released (discharged). In this manner, the pressure chamber 15 that receives the fluid sample 3 changes from the low-pressure space 7 to the high-pressure space 8, the fluid sample 3 is pressurized, and the cells contained in the fluid sample 3 are thus disrupted. Moreover, the fluid sample 3 is pushed into the release channel 9 and receives shear stress when passing through the precision orifice 4, and cell disruption is thus promoted. The fluid sample 3 that has passed through the release channel 9 suddenly expands when discharged under the atmospheric pressure to thereby further promote cell disruption and is then collected in a collecting container, for example. According to the third pyrotechnic cell disruption apparatus D3 in the present embodiment, it is also possible to obtain effects similar to those of the first and second pyrotechnic cell disruption apparatuses D1 and D2.

Fourth Embodiment

Figure 7:
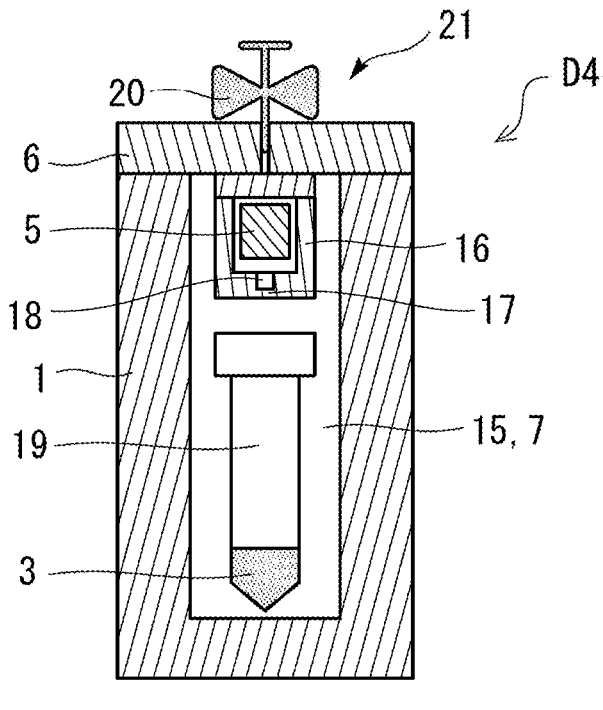
FIG. 7 illustrates a schematic sectional view of a fourth pyrotechnic cell disruption apparatus in a first configuration prior to pressurizing.
Figure 8:
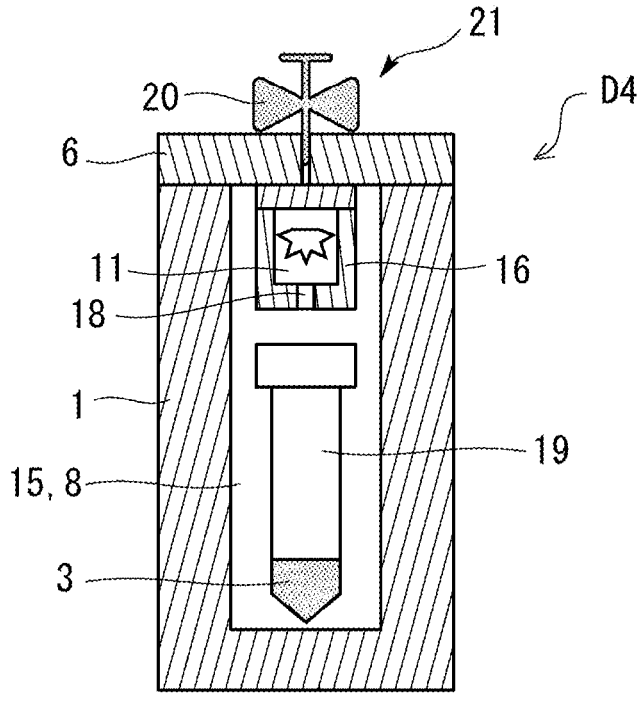
FIG. 8 illustrates a schematic sectional view of the fourth pyrotechnic cell disruption apparatus in a second configuration after pressurizing.

FIG. 7 illustrates a schematic sectional view of a fourth pyrotechnic cell disruption apparatus in a first configuration prior to pressurizing and FIG. 8 illustrates a schematic sectional view of the fourth pyrotechnic cell disruption apparatus in a second configuration after pressurizing. In contrast to the embodiments illustrated in FIGS. 1-6, the embodiment illustrated in FIGS. 7-8 does not have an orifice, but includes a hermetically sealed pressure chamber 15 forming the low-pressure space 7 prior to the condition of the pyrotechnic charge, while the exact same space forms the high-pressure space 8 after ignition, the latter configuration illustrated in FIG. 8. The sample size can be the same as in FIGS. 1-6, for instance 1 ml, 150 μL or 10 μL. The fluid sample 3 is provided according to this embodiment in a separate sample container 19. In addition, the container includes a pressure relief 21, in this embodiment comprising a pressure release valve 20. The container 19 is of sufficient flexibility so that it can collapse under the pressure and therefore pressurize the fluid sample 3. For instance, the container may be formed as a sample pouch, see for instance FIG. 9. In the alternative, if the container 19 is filled in its entirety with the fluid sample 3, not including any gas, it may not collapse since the fluid sample 3 provides support, but should still have sufficient flexibility for pressurizing the sample. Apart from accommodating the sample, the container 19 may also contain a different material, for instance a water absorbent polymer—which could help protect the integrity of the container when exposed to the pressure shock wave resulting from the combustion of the pyrotechnic charge 5. Conversely, if desired, the container can be configured so that it ruptures under the pressure from the pyrotechnic charge. One or more samples (pouches) could be simultaneously processed in the same chamber.

After quickly pressurizing upon ignition and combustion of the pyrotechnic charge 5, the pressure release valve 20 is opened at an effective time for the cell disruption after the fluid sample 3 has been exposed to the sudden pressure increase by the gas pressure generated from the pyrotechnic charge 5. Opening of the pressure release valve 20 also typically happens quickly, generating a rapid pressure reduction over time, facilitating rupturing of the cell membrane due to cell expansion. The heat generated by the pyrotechnic charge 5 may help make the cell membrane more vulnerable to rupture and therefore help with the cellular disruption. Various other physical and chemical conditions resulting from the combustion of the pyrotechnic charge 5 may contribute to the cell disruption. The composition of charge (explosive) itself, but also possibly an initiator-gas generator combination, can be applied to adjust the speed of gas and heat generation. The waste heat may be used for other purposes within a Point of Care (POC) detection system (amplification and detection). Waste gas pressure can be used or stored for use in a POC device to move the sample from one stage to another.

The concept of the container 19 helps complying with various regulatory standards to clinical laboratory testing since the operating personnel is protected from exposure by the sample. Depending on the material from which the container 19 is formed and the filling volume of the container by the sample, the container might rupture under the pressure, or stay intact.

The fluid sample 3 can be removed from the apparatus by either opening cap 6, or releasing through the pressure release valve 20 if the container 19 is configured to be ruptured. Such release of the disrupted cell sample can be accomplished by turning the device around and using some residual pressure for releasing the sample.

An advantage of this hydrostatic pressure shock is minimizing seals and moving parts. It would also be possible to provide a spring or configure the housing so that it may elastically deform and spring back, creating a pressure wave resonating at a specific frequency and amplitude, increasing the extent of cell lysis before releasing (discharging) the pressure.

Using pyrotechnic cell disruption creates enough shear stress and has a rapid enough decompression that this embodiment allows that the sample wouldn't need to be pushed through a precision orifice. This offers many more advantages than simply replacing large equipment such as the prior art French Press with pyrotechnic cell disruption. Specifically, the entire sample preparation and assay could occur in a single chamber of the apparatus; a hydrostatic process. The apparatus would be simpler in structure and likely have fewer parts. This would probably decrease the cost of development and manufacturing, as well as pose less risk of mechanical failure and contamination. It might also require less sample volume and/or improve assay signal by preventing sample waste.

A fourth pyrotechnic cell disruption apparatus D4 (see FIGS. 7 and 8) configured as described above includes: the pyrotechnic charge 5 configured to be ignited and to combust upon ignition; the pressure chamber 15 (low-pressure space 7/high-pressure space 8) configured to receive the fluid sample 3 and to be pressurized upon the ignition and the combustion of the pyrotechnic charge 5; and the pressure relief 21 (pressure release valve 20) that releases a pressure from the pressure chamber 15 after the pressure chamber 15 is pressurized by the ignition and the combustion of the pyrotechnic charge 5. As is obvious from FIG. 7, the structure of the pyrotechnic charge chamber housing 16 that receives the pyrotechnic charge 5 before operations (before pressurizing) of the fourth pyrotechnic cell disruption apparatus D4 is similar to those of the second and third pyrotechnic cell disruption apparatuses D2 and D3, the pyrotechnic charge chamber housing 16 is provided with the pressure release channel 18 and the breaking point 17, which are formed inside the pyrotechnic charge chamber housing 16 configured to rupture upon the ignition and the combustion of the pyrotechnic charge 5 and is received in the different pyrotechnic charge chamber 11 that is separated from the pressure chamber 15. Also, in the fourth pyrotechnic cell disruption apparatus D4, the breaking point 17 ruptures due to a pressure of combustion gas generated by the pyrotechnic charge 5 being ignited upon operations, and the pyrotechnic charge chamber housing 16 (pyrotechnic charge chamber 11) opens directly to the pressure chamber 15 (low-pressure space 7) similarly to the third pyrotechnic cell disruption apparatus D3. As a result, the combustion gas of the pyrotechnic charge 5 flows out from the pyrotechnic charge chamber housing 16 into the pressure chamber 15 where the container 19 that holds (receives) the fluid sample 3 is disposed, and the inside of the pressure chamber 15 changes from the low-pressure space 7 to the high-pressure space 8. In this manner, the fluid sample 3 received in the container 19 is pressurized, and it is thus possible to disrupt the cells contained in the fluid sample 3.

Also, in the fourth pyrotechnic cell disruption apparatus D4, the container 19 is formed by a pouch that has flexibility and can be filled with (receive) the fluid sample 3, for example, and the pouch is configured not to rupture when exposed to a pressure upon ignition and combustion of the pyrotechnic charge. It is thus possible to suitably pressurize the fluid sample 3 with which the container 19 is filled and to disrupt the cells without breaking the container 19 upon operations of the fourth pyrotechnic cell disruption apparatus D4.

In the fourth pyrotechnic cell disruption apparatus D4, the pressure relief 21 includes the pressure release valve 20, and the pressure release valve 20 may be a valve body that is automatically opened at a timing when a predetermined elapse time elapses after ignition of the pyrotechnic charge 5 upon operations of the fourth pyrotechnic cell disruption apparatus D4, for example. Alternatively, the pressure release valve 20 of the pressure relief 21 may be a valve body that is automatically opened when the pressure in the pressure chamber 15 (high-pressure space 8) that receives the container 19 rises to a predetermined pressure upon operations of the fourth pyrotechnic cell disruption apparatus D4, for example. Although a setting value of the pressure at which the pressure release valve 20 is automatically opened is not particularly limited, the pressure release valve 20 may be set such that it is opened when exposed to a pressure of at least 20,000 psi. The setting value of the pressure at which the pressure release valve 20 is automatically opened can be appropriately set in accordance with the amount of fluid sample 3 received in the container 19 and the type of the cells contained in the fluid sample 3, for example. Also, the pressure release valve 20 may be a valve body that can be manually opened. Additionally, the pressure relief 21 may include a rupture plate that ruptures when exposed to a predetermined pressure. The rupture plate may be configured to rupture when exposed to a pressure of at least 20,000 psi, for example.

As described above, once the pressure release valve 20 is opened from a state in which the fluid sample 3 received in the pressure chamber 15 (high-pressure space 8) is pressurized under a high pressure, a sudden pressure drop occurs in the high-pressure space 8. As a result, the cells contained in the fluid sample 3 suddenly expand, large shear stress, for example, acts on the cells, and it is thus possible to promote cell disruption. Note that although the material of the container 19 that is filled with (receives) the fluid sample 3 is not particularly limited, a flexible pouch that has flexibility may be used. Alternatively, the container 19 may be formed of a hard material such as a resin, a glass, or the like. In this case, the container 19 may collapse or break, and the fluid sample 3 therein may be pressurized, when the pressure chamber 15 changes from the low-pressure space 7 to the high-pressure space 8 due to the combustion gas of the pyrotechnic charge 5.

Fifth Embodiment

Figure 9:
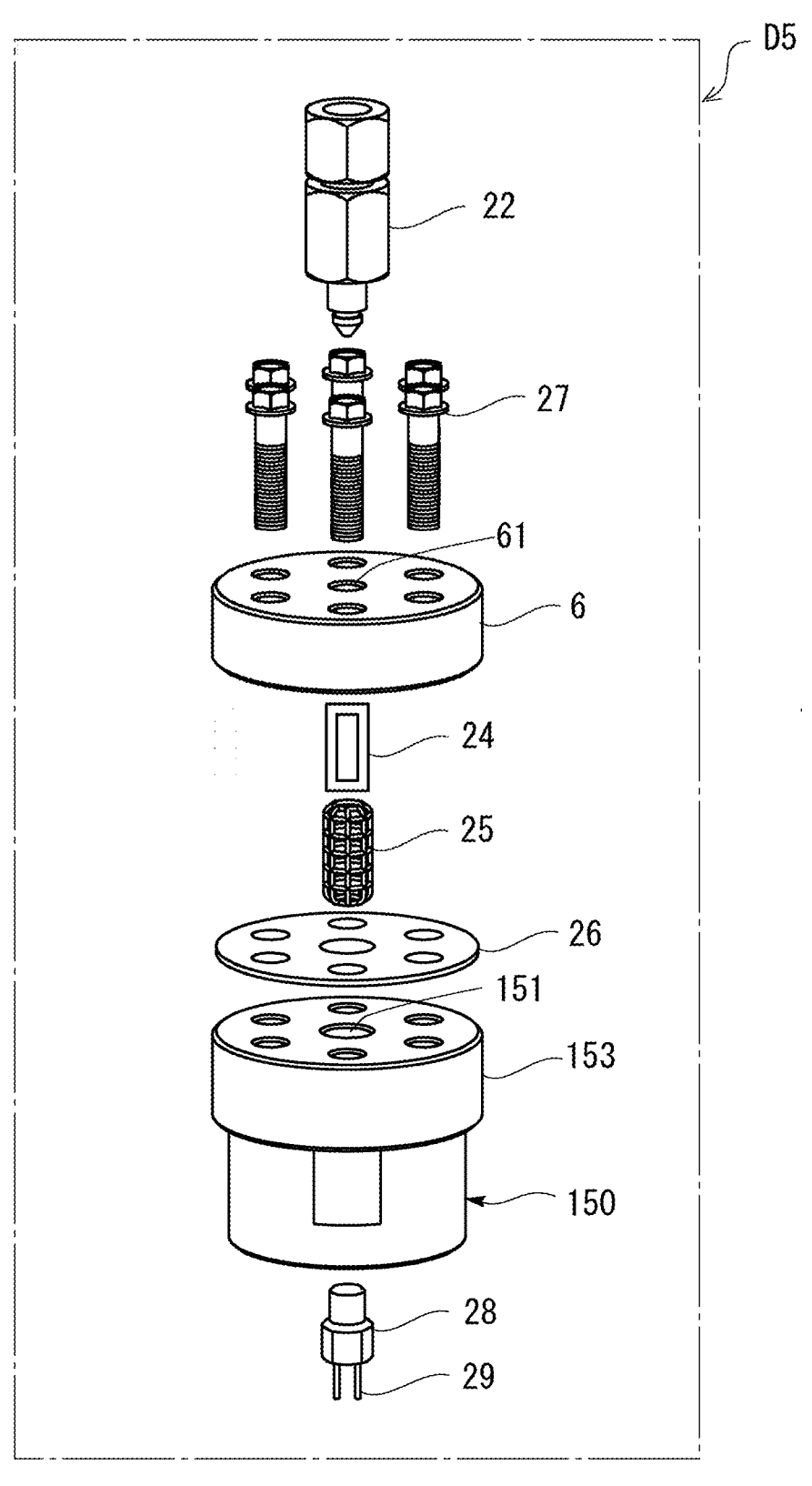
FIG. 9 illustrates an exploded view of a fifth embodiment of a pyrotechnic cell disruption apparatus.
Figure 10:
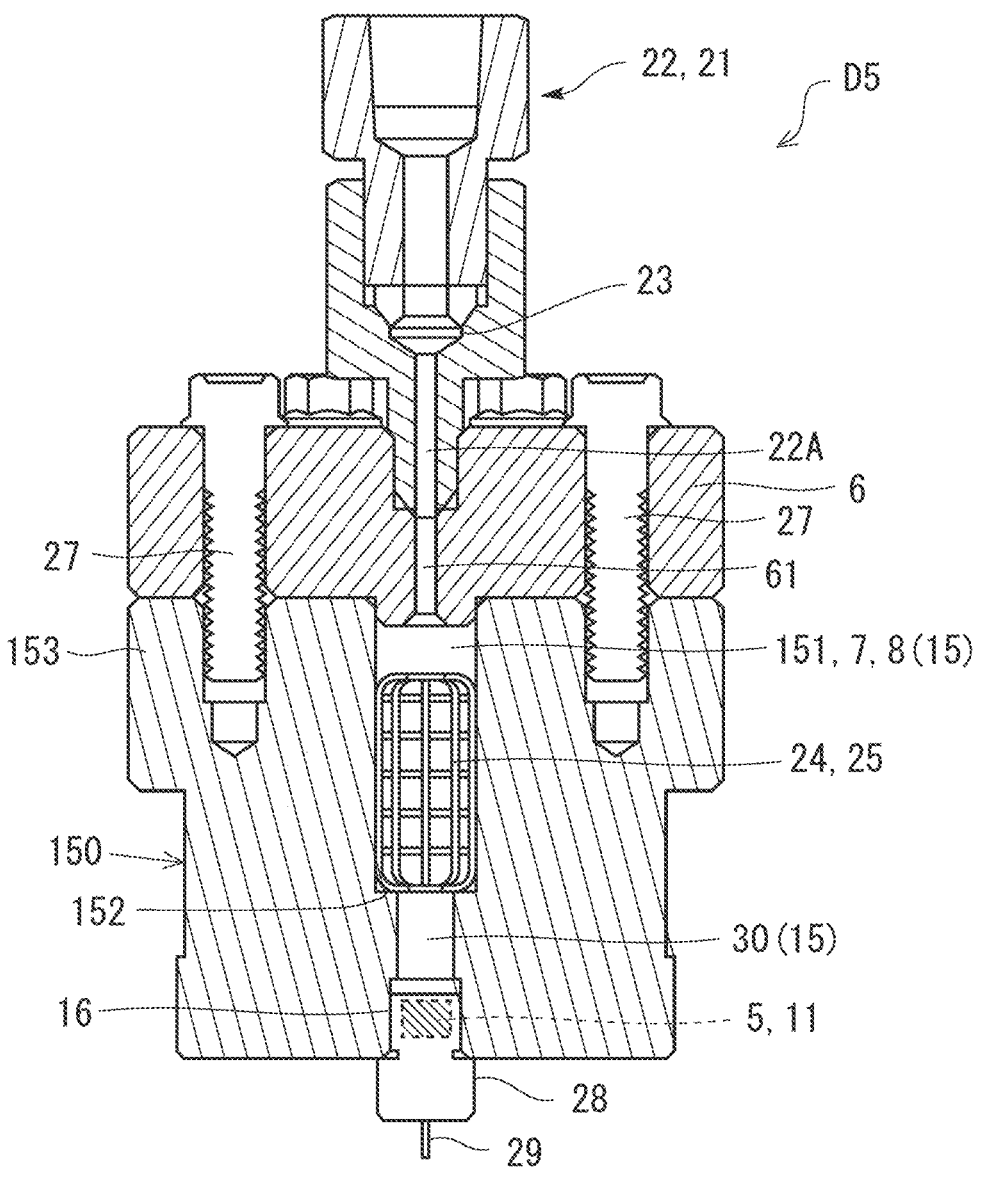
FIG. 10 illustrates a schematic sectional view of the fifth embodiment of a pyrotechnic cell disruption apparatus.

FIG. 9 illustrates an exploded view of a fifth pyrotechnic cell disruption apparatus and FIG. 10 illustrates a schematic sectional view of the fifth pyrotechnic cell disruption. The pressure relief 21 is formed as a rupture disc assembly 22 including a rupture disc 23 as illustrated in FIG. 10. This rupture disc provides quick release of the pressure in a controlled fashion and within the time frame needed for rupturing the rupture disc 23, wherein the rupture disc is designed to allow such time frame as needed to achieve cell lysis. The sample pouch 24 is provided in a sample cage 25. Although this cage 25 is not absolutely necessary, it helps handling the sample pouch 24 with care and helps with inserting it into the pressure chamber 15. The cage also prevents the sample pouch from accidentally blocking the pressure relief vent pathway once the pyrotechnical charge has been detonated. If this were to happen, the sample could potentially be aerosolized and blown into the surroundings. This is further mitigated by the embodiment illustrated in FIGS. 11 and 12, which places the sample out of the direct path between the gas generated by the pyrotechnic charge and the vent. Assembly of the apparatus can be accomplished by screwing together the pressure chamber 15 with the inserted sample pouch 24 within the cage 25, a gasket 26, and the cap 6 by means of high-strength bolts 27 or other clamping methods. The pyrotechnic charge is provided within an initiator 28 that is coaxially inserted into the pressure chamber 15. Ignition of the pyrotechnic charge can be accomplished by connecting the initiator 28 through its wires 29 to an electric power source providing a sufficient voltage for igniting the pyrotechnic charge within the initiator 28.

A fifth pyrotechnic cell disruption apparatus D5 according to a fifth embodiment is an apparatus that more specifically realize the concept of the fourth pyrotechnic cell disruption apparatus D4 described in FIGS. 7 and 8. In the fifth embodiment, similar reference signs will be used for similar elements as compared with the fourth embodiment. As illustrated in FIG. 10, the pressure chamber 15 includes a pressure container 150, and a hollow portion is provided to penetrate through the pressure container 150 in the up-down direction of the pressure container 150. The initiator 28 is attached to a portion where the hollow portion opens at the bottom of the pressure container 150 to block the opening in an air tight manner. As illustrated in FIG. 10, the pyrotechnic charge chamber housing 16 of the initiator 28 is disposed to face the inside of the pressure container 150.

A reference sign 153 illustrated in FIG. 9 denotes a cap fastening portion in the pressure container 150. In the example illustrated in FIG. 9, a cap fastening portion 153 is located on the upper side of the pressure container 150, such that the cap 6 can be detachably attached. A screw hole into which a high-strength bolt 27 is inserted is formed in the cap fastening portion 152, the gasket 26, and the cap 6. It is possible to fasten the cap 6 integrally to the cap fastening portion 153 of the pressure container 150 by sandwiching the gasket 26 between the pressure container 150 and the cap 6 and screwing the high-strength bolt 27 inserted into each screw hole, and on the contrary, it is possible to separate the cap 6 from the pressure container 150 by removing the high-strength bolt 27. The pressure chamber 15 in an air tight state is formed inside the pressure container 150 by the cap 6 being attached to the pressure container 150.

The pressure chamber 15 in the present embodiment extends in the up-down direction (axial direction) of the pressure container 150 and includes a sample container receiving unit 151 and a pressure channel 30 that are coaxially connected. As illustrated in FIGS. 9 and 10, the sample container receiving unit 151 opens in the upper surface of the pressure container 150, and the lower end of the sample container receiving unit 151 is connected to the upper end of the pressure channel 30. The pressure channel 30 and the sample container receiving unit 151 are cavities with columnar shapes, for example, the diameter (cross-sectional area) of the sample container receiving unit 151 is slightly larger than the diameter (cross-sectional area) of the pressure channel 30, and the sample container placement unit 152 is formed by a level difference provided at the connected portion (boundary portion) between the sample container receiving unit 151 and the pressure channel 30 and extending in the radial direction. It is possible to place the sample pouch 24 alone or the sample pouch 24 in a state in which a cage 25 is attached thereto on the sample container placement unit 152. It is thus possible to stably receive the sample pouch 24 in the pressure chamber 15. Note that the cage 25 is a basket-like member capable of holding the sample pouch 24 with flexibility, for example. The sample pouch 24 is maintained in a partially exposed state even in a state in which the cage 25 is attached to the sample pouch 24. Note that although the example in which the fluid sample is received in the flexible sample pouch 24 has been described in the present embodiment, another container filled with the fluid sample may be placed on the sample container placement unit 152 and may be received in the sample container receiving unit 151.

Also, the pyrotechnic charge chamber 11 that receives the pyrotechnic charge 5 is formed inside the pyrotechnic charge chamber housing 16 in the initiator 28. The pyrotechnic charge chamber housing 16 is disposed in the pressure channel 30. The pyrotechnic charge chamber housing 16 may be formed of a cup member that can rupture due to energy at the time of ignition and combustion of the pyrotechnic charge 5, for example. The cup member may be formed of a thin metal member such as aluminum, for example. In this manner, the pyrotechnic charge chamber 11 opens directly to the pressure channel 30 in the pressure chamber 15 due to the energy at the time of the ignition and the combustion of the pyrotechnic charge 5, and the combustion gas of the pyrotechnic charge 5 can thus be introduced into the pressure channel 30. The pressure channel 30 functions as a vent pathway for supplying the combustion gas of the pyrotechnic charge 5 to the sample container receiving unit 151 when the initiator 28 operates. Note that before operations of the fifth pyrotechnic cell disruption apparatus D5, the pressure chamber 15 (the pressure channel 30 and the sample container receiving unit 151) is formed as the low-pressure space 7 at a low pressure.

As illustrated in FIGS. 9 and 10, the sample container receiving unit 151 is opened in the upper surface of the pressure container 150 and is configured such that the sample container receiving unit 151 is covered with the cap 6 by the cap 6 being attached to the pressure container 150. As illustrated in FIGS. 9 and 10, the cap 6 is provided with the pressure relief 21. The pressure relief 21 includes the rapture disc assembly 22 and a pressure relief vent pathway 61. The pressure relief vent pathway 61 is a vent pathway formed to penetrate through the cap 6 in the axial direction. The rupture disc assembly 22 includes a pressure relief vent pathway 22A connected to the pressure relief vent pathway 61, a rupture disc 23 disposed to block (close) a midpoint of the pressure relief vent pathway 22A, and the like. The pressure relief vent pathway 22A extends to penetrate through the rupture disc assembly 22 in the up-down direction. The pressure relief vent pathways 61 and 22A cause the sample container receiving unit 151 and the exterior space to communicate and opens the pressure in the pressure chamber 15 to the outside when the rupture disc 23 ruptures after the pressure chamber 15 is pressurized by the ignition and the combustion of the pyrotechnic charge 5. The rupture disc 23 is configured such that the rupture disc 23 ruptures at a timing when a primary-side pressure, that is, the pressure in the pressure chamber 15 rises to a predetermined pressure. The pressure at which the rupture disc 23 ruptures can be appropriately set in accordance with the amount of fluid sample 3 with which the sample pouch 24 is filled and the type of cells contained in the fluid sample 3, for example. As illustrated in FIG. 10, the pressure channel 30, the sample container receiving unit 151, and the pressure relief vent pathways 61 and 22A are coaxially disposed in the state in which the cap 6 is attached to the pressure container 150. More specifically, the pressure channel 30, the sample container receiving unit 151, and the pressure relief vent pathways 61 and 22A are coaxially disposed such that they are aligned on one straight line passing through the center axis of the pressure container 150 in the state in which the cap 6 is attached to the pressure container 150.

According to the fifth pyrotechnic cell disruption apparatus D5 configured as described above, once the pyrotechnic charge 5 is ignited by operating the initiator 28, the inner pressure of the pyrotechnic charge chamber 11 rises due to combustion gas generated by combustion of the pyrotechnic charge 5, and the pyrotechnic charge chamber housing 16 (a cup member, for example) splits. As a result, the combustion gas of the pyrotechnic charge 5 is introduced from the pyrotechnic charge chamber 11 to the pressure channel 30 in the pressure chamber 15. Then, the combustion gas of the pyrotechnic charge 5 is introduced into the sample container receiving unit 151 of the pressure chamber 15 coaxially connected to the pressure channel 30, and as a result, the pressure of the sample container receiving unit 151 that receives the sample pouch 24 suddenly increases. In this manner, the sample container receiving unit 151 changes from the low-pressure space 7 to the high-pressure space 8 at a high pressure. As for the sample pouch 24, a part of the sample pouch 24 is exposed even in a state in which the cage 25 is attached thereto. In this manner, it is possible to expose the sample pouch 24 to a high pressure inside the sample container receiving unit 151 that has changed to the high-pressure space 8. As a result, the fluid sample 3 filling the sample pouch 24 is suddenly pressurized, and the cells contained in the fluid sample 3 can be disrupted. Moreover, once the rupture disc 23 ruptures at the timing when the pressure in the sample container receiving unit 151 rises to the predetermined pressure, then the sample container receiving unit 151 is quickly decompressed. As a result, the cells contained in the fluid sample 3 filling the sample pouch 24 suddenly expands, large shear stress acts on the cells, for example, and cell disruption is thus further promoted. Note that the configuration in which the pressure relief vent pathway 22A of the pressure relief 21 is blocked by the rupture disc 23 (rupture plate) is employed in the above example, this may be replaced with the pressure release valve 20 described in the fourth embodiment. In other words, the pressure release valve 20 may be automatically opened at the timing when predetermined elapse time elapses after the ignition of the pyrotechnic charge 5, or the pressure release valve 20 may be automatically opened at the timing when the pressure in the pressure chamber 15 rises to the predetermined pressure.

Note that according to the fifth pyrotechnic cell disruption apparatus D5, the pressure channel 30 and the sample container receiving unit 151 are coaxially disposed, and it is thus possible to smoothly introduce the combustion gas to the sample container receiving unit 151 via the pressure channel 30 when the initiator 28 is operated to combust the pyrotechnic charge 5, and thereby to quickly disrupt the cells contained in the fluid sample 3 filling the sample pouch 24. Moreover, according to the fifth pyrotechnic cell disruption apparatus D5, the pressure channel 30, the sample container receiving unit 151, and the pressure relief vent pathways 61 and 22A are coaxially disposed in the state in which the cap 6 is attached to the pressure container 150, and it is thus possible to smoothly discharge the combustion gas from the inside of the pressure chamber 15 (the sample container receiving unit 151 and the pressure channel 30) to the outside through the pressure relief vent pathways 61 and 22A when the rupture disc 23 ruptures after the initiator 28 operates. It is thus possible to decompress the pressure chamber 15 in a shorter time. As a result, the cells contained in the fluid sample 3 in the sample pouch 24 more suddenly expand, and it is possible to further promote the cell disruption.

Sixth Embodiment

Figure 11:
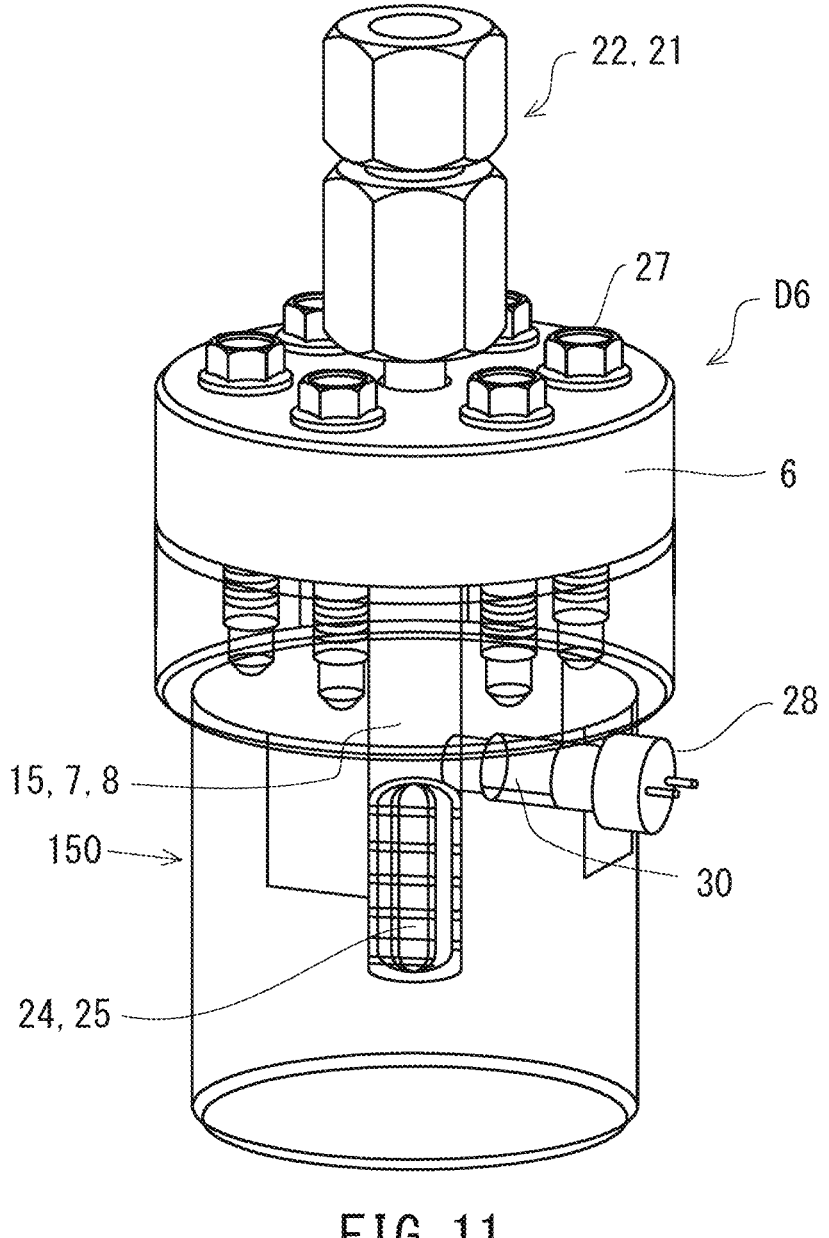
FIG. 11 illustrates a perspective see-through view of a sixth embodiment of a pyrotechnic cell disruption apparatus.
Figure 12:
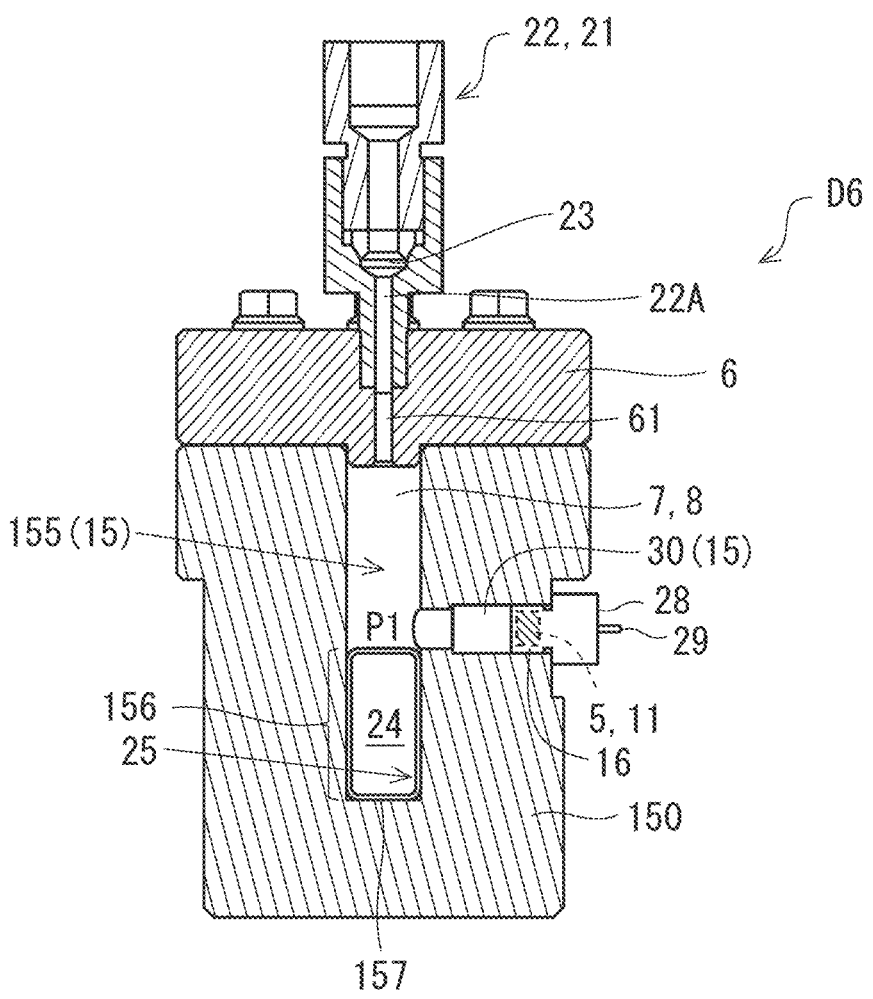
FIG. 12 illustrates a schematic sectional view of the sixth embodiment of a pyrotechnic cell disruption apparatus.

FIG. 11 illustrates a perspective see-through view of a sixth embodiment of a pyrotechnic cell disruption apparatus and FIG. 12 illustrates a schematic sectional view of the sixth pyrotechnic cell disruption apparatus. This sixth embodiment is very similar to the fifth embodiment. However, the initiator 28 is positioned laterally, connecting in a radial direction to the pressure chamber 15 via a pressure channel 30 with the low-pressure space/high-pressure space 7, 8. An advantage of this lateral approach according to FIGS. 11 and 12 in comparison to the coaxial approach according to FIGS. 9 and 10 is that the sample pouch 24 within the sample cage 25 is not directly exposed to the gas flow from the initiator 28 after the ignition of the pyrotechnic charge. Also, the pressure channel 30 may intersect the low-pressure space/high-pressure space 7, 8 spaced beyond one axial end of the sample pouch 24/sample cage 25 combination, while the other axial end of the sample pouch 24/sample cage 25 combination may rest on the bottom of the pressure chamber 15. Apart from avoiding direct exposure of the sample pouch 24/sample cage 25 combination from the gas stream, the pressure generated by the pyrotechnic charge also presses down on the sample pouch 24/sample cage 25 combination towards the bottom of the pressure chamber 15 and therefore holds the sample pouch 24/sample cage 25 combination firmly in place, avoiding undesired movement of the sample pouch 24/sample cage 25 combination.

A pyrotechnic cell disruption apparatus D6 according to a sixth embodiment is a modification example of the fifth pyrotechnic cell disruption apparatus D5. In the sixth embodiment, similar reference signs will be used for similar elements as compared with the fifth embodiment. In the sixth pyrotechnic cell disruption apparatus D6, the pressure container 150 has a bottomed cylinder shape, and the pressure chamber 15 is formed therein. The pressure chamber 15 includes the pressure channel 30 that extends in the first direction, is then connected to the pressurized space unit 155, branches in the second direction different from the first direction from the midpoint of the pressurized space unit 155, and is then connected to the pressurized space unit 155. In the example illustrated in FIGS. 11 and 12, the pressurized space unit 155 extends in the up-down direction (the axial direction, the first direction) of the pressure container 150, the pressure channel 30 extends in the horizontal direction (radial direction) of the pressure container 150, and the pressure channel 30 branches in the perpendicular direction from the pressurized space unit 155. Note that the pressure chamber 15 is formed as the low-pressure space 7 before operations of the sixth pyrotechnic cell disruption apparatus D6, and is formed as the high-pressure space 8 after operations.

Also, the sixth pyrotechnic cell disruption apparatus D6 includes the pressure relief 21 similar to that in the fifth pyrotechnic cell disruption apparatus D5 at the cap 6. The pressure relief 21 includes the rapture disc assembly 22 and the pressure relief vent pathway 61. The pressurized space unit 155 includes a proximal end and a distal end relative to the pressure relief 21, and the distal end 155B is located at the bottom 157 of the pressure container 150. On the other hand, the proximal end of the pressurized space unit 155 opens in the upper surface of the pressure container 150 and is configured such that the pressurized space unit 155 is covered with the cap 6 by the cap 6 being attached to the pressure container 150. Also, a configuration in which the proximal end of the pressurized space unit 155 is connected to the pressure relief vent pathway 61 in a state in which the cap 6 is attached to the pressure container 150 is employed. For example, the pressurized space unit 155 and the pressure relief vent pathway 61 are coaxially disposed through the center axis of the pressure container 150.

The pressurized space unit 155 includes the sample container receiving unit 156 for receiving the sample pouch 24 between the portion 155C connected to the pressure channel 30 and the distal end. In other words, the pouch holding unit 156 indicates a region located further downward than the connected portion P1 in the pressurized space unit 155. In the present embodiment, it is possible to place the sample pouch 24 to which the cage 25 is attached on the bottom 157 of the pressure container 150. It is a matter of course that the sample pouch 24 alone may be placed on the bottom 157 of the pressure container 150. Note that the height of the sample container receiving unit 156 has a dimension that is equal to or greater than the height of the sample pouch 24, such that the sample pouch 24 does not project to the side of the connected portion P1 in the state in which the sample pouch 24 is received in the sample container receiving unit 156. In other words, it is possible to receive the sample pouch 24 in the sample container receiving unit 156 such that the upper end of the sample pouch 24 is located further downward than the portion P1 of the pressurized space unit 155 connected to the pressure channel 30. As illustrated in FIGS. 11 and 12, the initiator 28 is attached to a side surface of the pressure container 150, and the initiator 28 is disposed in the horizontal direction such that the pyrotechnic charge chamber housing 16 of the initiator 28 faces the inside of the pressure channel 30. In other words, the pyrotechnic charge 5 of the initiator 28 is disposed in the pressure channel 30.

According to the sixth pyrotechnic cell disruption apparatus D6 configured as described above, further effects described below are obtained as compared with effects similar to those described in regard to the fifth pyrotechnic cell disruption apparatus D5. In other words, according to the sixth pyrotechnic cell disruption apparatus D6 in the present embodiment, combustion gas generated by the pyrotechnic charge 5 being ignited and combusted upon operations of the initiator 28 is supplied to the pressurized space unit 155 via the pressure channel 30, and the pressurized space unit 155 thus changes from the low-pressure space 7 at a low pressure to the high-pressure space 8 at a high pressure. At that time, the pressure caused by the combustion gas flowing into the sample container receiving unit 156 on the lower side from the connected portion P1 pushes the sample pouch 24 to which the sample cage 25 is attached toward the bottom of the pressure container 150, and it is thus possible to stably hold the sample pouch 24 in a pressurized state in the sample container receiving unit 156. Also, since the upper end of the sample pouch 24 is located further downward than the connected portion P1 in the pressurized space unit 155, it is possible to curb direct exposure of the sample pouch 24 to the combustion gas flow from the pyrotechnic charge 5.

Also, when the rupture disc 23 in the rupture disc assembly 22 ruptures, the pressure chamber 15 communicates with the exterior space, and the pressure in the pressure chamber 15 is thus released (discharged) to the outside through the pressure relief vent pathways 61 and 22A. At that time, since a most part of the gas discharged from the pressure chamber 15 to the outside via the pressure relief vent pathways 61 and 22A does not pass through the sample container receiving unit 156, it is thus possible to stably leave the sample pouch 24 on the bottom of the pressure container 150 when the pressure in the pressure chamber 15 is released. In this manner, it is possible to curb movement of the sample pouch 24 from the sample container receiving unit 156 to the upper side and closure of the pressure relief vent pathway 61 with the sample pouch 24, for example, and thereby to curb inhibition of quick and smooth decompression of the pressure chamber 15. Although the example in which the fluid sample is received in the flexible sample pouch 24 has been described in the present embodiment, another container filled with the fluid sample may be received in the sample container receiving unit 156.

Seventh Embodiment

Figure 13:
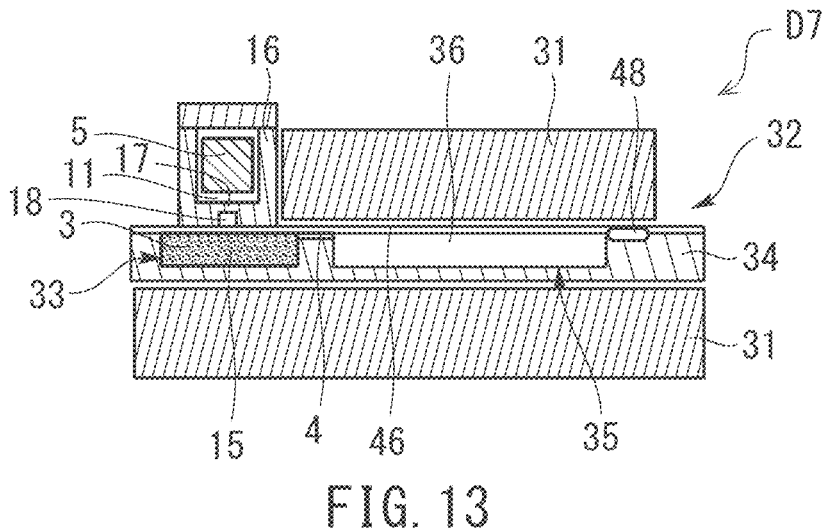
FIG. 13 illustrates a schematic sectional view of a seventh embodiment of a pyrotechnic cell disruption apparatus including a sample chip.
Figure 14:
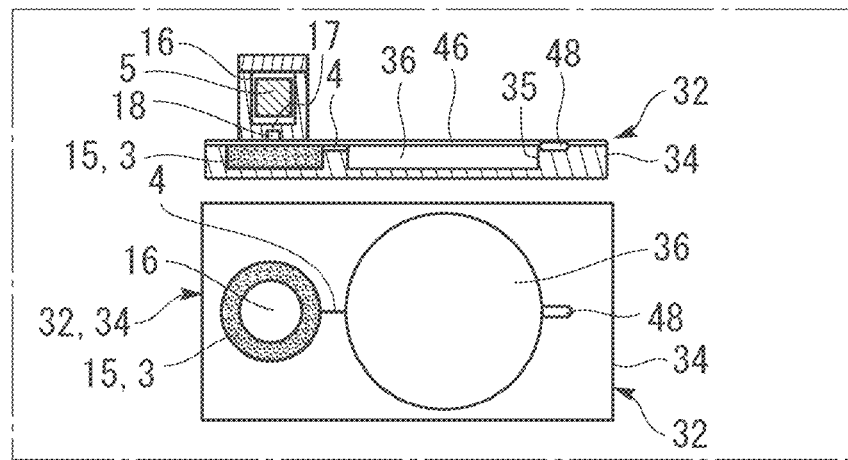
FIG. 14 illustrates a sectional view like FIG. 13 without clamps and a plan view in a first configuration prior to pressurizing.
Figure 15:
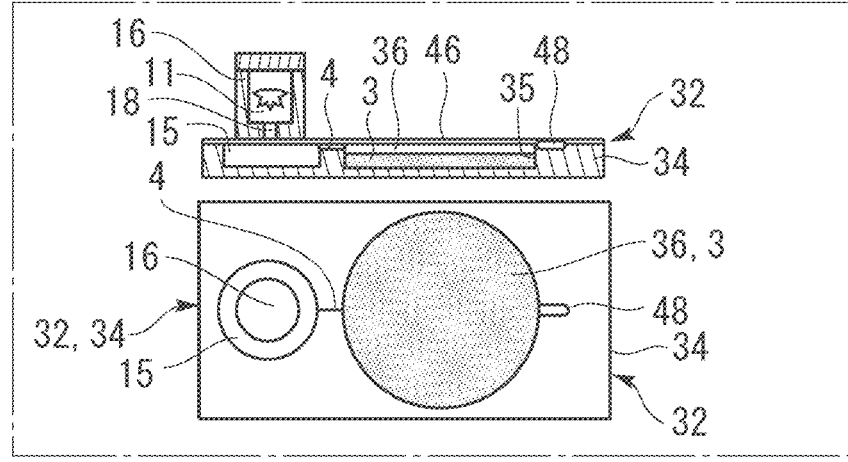
FIG. 15 illustrates a sectional view like FIG. 13 without clamps and a plan view in a second configuration after pressurizing.

FIGS. 13-15 demonstrate a seventh embodiment of a pyrotechnic cell disruption apparatus including a sample chip. As illustrated in FIG. 13, clamps 31 are provided on the top and on the bottom of a chip 32 holding the fluid sample 3 in a first recess 33 formed within a substrate 34 and a second recess 35 in the substrate 34, forming an expansion chamber 36. The pyrotechnic charge chamber housing 16 can be integrally formed with one of the clamps 31 or may be provided separately. The pressure release channel 18 may be provided centrally on top of the fluid sample 3 when the chip is in its clamped position between clamps 31. The pressure chamber 15 is sealed with respect to the environment by the clamp and/or the pyrotechnic charge chamber housing 16 or a combination thereof. The precision orifice 4 connects the pressure chamber 15 and the expansion chamber 36 with each other. Such precision orifice 4 may for instance be created by a groove in the substrate 34 that is closed by the clamp to form a closed channel between the pressure chamber 15 and the expansion chamber 36. A thin film may be bonded to the chip 34, sealing off the precision orifice 4, the expansion chamber, and the pressure chamber. A small hole in the film or a frangible section may be provided for pressurizing by the pyrotechnic charge. Other forms of orifice are possible, for instance running entirely through the substrate 34.

FIG. 14 demonstrates the state prior to ignition while FIG. 15 demonstrates the configuration after ignition and movement of the fluid sample 3 from the pressure chamber 15 into the expansion chamber 36. This has been demonstrated by the fluid sample 3 illustrated in black in FIG. 14 now being dispersed in FIG. 15 over the expansion chamber 36 from where the material from within the disrupted cells can be collected.

As described above, a seventh pyrotechnic cell disruption apparatus D7 (see FIGS. 13 to 15) according to a seventh embodiment includes a chip 32 (pyrotechnic cell destruction chip) including the substrate 34, the pressure chamber 15 that is formed by the first recess 33 formed in the substrate 34, the expansion chamber 36 that is formed by the second recess 35 formed in the substrate 34, and the like. In the present embodiment, similar reference signs will be used for similar elements as compared with the aforementioned embodiments. In the example illustrated in FIG. 13, the first recess 33 (pressure chamber 15) and the second recess 35 (expansion chamber 36) are formed to open on the upper surface side of the substrate 34, and the first recess 33 (pressure chamber 15) and the second recess 35 (expansion chamber 36) are connected with the precision orifice 4 (first channel). The precision orifice 4 may be formed by an opening groove that opens in the upper surface of the substrate 34. In the example illustrated in FIG. 13, the upper surface of the substrate 34 is covered with a thin top layer film 46. For example, the top layer film 46 may be caused to adhere to the upper surface of the substrate 34, and it is possible to tightly close the pressure chamber 15, the expansion chamber 36, and the precision orifice 4 from the outside by sealing the opening groove for forming the first recess 33, the second recess 35, and the precision orifice 4 with the top layer film 46. Here, various polymer films can be used as the top layer film 46 and a bottom layer film 47, which will be described later, the top layer film 46 and the bottom layer film 47 may be formed by combining or laminating polypropylene (PP), polyethylene (PE), and other thermoplastic resins, for example, and it is also possible to use films to which heat shrinkability, hydrophilicity, or hydrophobicity are applied as needed.

The seventh pyrotechnic cell disruption apparatus D7 is further clamped by a pair of clamps 31 disposed at the upper portion (top) and the lower portion (bottom) of the chip 32 (pyrotechnic cell destruction chip). The pair of clamps 31 are high-strength clamps with rigidity, for example, and can be detachably assembled with the chip 32. The seventh pyrotechnic cell disruption apparatus D7 further includes the pyrotechnic charge chamber housing 16 that forms the pyrotechnic charge chamber 11, the pyrotechnic charge 5 that is received in the pyrotechnic charge chamber 11, and the like, and as illustrated in FIG. 13, the pyrotechnic charge chamber housing 16 is disposed at an upper portion of the first recess 33 (pressure chamber 15) on the chip 32 (substrate 34). The pyrotechnic charge chamber housing 16 may be formed integrally with the clamp 31 that clamps the upper side of the chip 32 or may be separately provided.

Similarly to the second to fourth embodiments, the pressure release channel 18 and the breaking point 17 are formed at the bottom of the pyrotechnic charge chamber housing 16. The pressure release channel 18 is formed as a recess that opens to the outside of the pyrotechnic charge chamber housing 16, and the pressure release channel 18 is located at the center of the first recess 33 (pressure chamber 15) on the chip 32 (substrate 34). Also, the pyrotechnic charge chamber housing 16 is disposed such that the pressure release channel 18 is brought into close contact with the top layer film 46.

FIG. 14 illustrates a sectional view without the clamps and a plan view in the first configuration before pressurizing (before ignition of the pyrotechnic charge 5) of the seventh pyrotechnic cell disruption apparatus D7, and FIG. 15 illustrates a sectional view without the clamps and a plan view in the second configuration after pressurizing (after the ignition of the pyrotechnic charge 5). In each of FIGS. 14 and 15, the sectional view and the plan view are illustrated in the upper part and the lower part, respectively. The plan views illustrated at the lower parts in FIGS. 14 and 15 illustrate the top surface of the substrate 34 through the top layer film 46 in a see-through manner. Also, the fluid sample 3 is received in the pressure chamber 15 on the chip 32 before operations of the seventh pyrotechnic cell disruption apparatus D7. In FIG. 14, the fluid sample 3 received in the pressure chamber 15 is completely painted in black. On the other hand, once the seventh pyrotechnic cell disruption apparatus D7 operates, the pyrotechnic charge 5 is ignited, the pyrotechnic charge 5 combusts, and combustion gas is thus generated. In this manner, the pressure inside the pyrotechnic charge chamber 11 rises, the breaking point 17 of the pyrotechnic charge chamber housing 16 ruptures (splits), and the pressure release channel 18 of the pyrotechnic charge chamber housing 16 thus communicates with the pyrotechnic charge chamber 11. As a result, the portion of the top layer film 46 facing the pressure release channel 18 breaks due to the pressure inside the pyrotechnic charge chamber 11, and the combustion gas flows into the pressure chamber 15 on the chip 32. In this manner, the pressure chamber 15 on the chip 32 is suddenly pressurized, and the cells contained in the fluid sample 3 received in the pressure chamber 15 is disrupted. Note that a small hole or a vulnerable portion may be provided in advance at the portion of the top layer film 46 facing the pressure release channel 18. In this manner, it becomes easier to introduce the combustion gas of the pyrotechnic charge 5 into the pressure chamber 15 upon operations of the seventh pyrotechnic cell disruption apparatus D7.

Moreover, the fluid sample 3 is pushed into the precision orifice 4 by the pressure chamber 15 on the chip 32 being pressurized by the combustion gas of the pyrotechnic charge 5, and the fluid sample 3 that has moved to the expansion chamber 36 through the precision orifice 4 is held (collected) in the expansion chamber 36. When the fluid sample 3 passes through the precision orifice 4, large shear stress acts on the cells contained in the fluid sample 3, and the disruption of the cells is thus promoted. Here, the expansion chamber 36 has a larger volume than the pressure chamber 15, and the fluid sample 3 is decompressed when the fluid sample 3 flows from the pressure chamber 15 into the expansion chamber 36 through the precision orifice 4. According to this, it is possible to further promote the cell disruption by the fluid sample 3 suddenly expanding when the fluid sample 3 flows into the expansion chamber 36 through the precision orifice 4. The fluid sample 3 on which the cell disruption processing has been performed in this manner is collected in the expansion chamber 36. Also, the chip 32 in the present embodiment may include a ventilation hole 48 formed to establish communication between the expansion chamber 36 and the outside. The ventilation hole 48 may be formed by a groove opening in the upper surface of the substrate 34 and an opening in the top layer film 46 formed at a position overlapping the groove, for example. The ventilation hole 48 can perform ventilation to the outside through the opening in the top layer film 46 and the clearance between the top layer film 46 and the clamps 31 and can introduce the atmospheric pressure into the expansion chamber 36. In this manner, it is possible to further efficiently perform the disruption of the cells contained in the fluid sample 3 by setting the expansion chamber 36 under the atmospheric pressure and thereby causing the fluid sample 3 that has been transferred from the pressure chamber 15 to the expansion chamber 36 being more suddenly decompressed and expanded.

In the present embodiment, a reagent may be added to the fluid sample 3 collected in the expansion chamber 36, and a chemical reaction may be carried out in the expansion chamber 36. The reagent to be added to the fluid sample 3 is a reagent to cause a chemical reaction in the cells after the disruption contained in the fluid sample 3, and may be a reagent for achieving a polymerase chain reaction PCR, a loop-mediated isothermal amplification (LAMP), or any other isothermal amplification-related reactions, for example. The chip 32 in the present embodiment may further include the detection chamber formed in the form of a third recess in the substrate 34, and the expansion chamber 36 and the detection chamber may be connected with a channel. Also, after the reagent is added to the fluid sample 3 in the expansion chamber 36 to carry out a chemical reaction, the fluid sample 3 after the reaction processing may be discharged from the expansion chamber 36 to the detection chamber via the channel. Additionally, a plurality of types of reagents may be added to the fluid sample 3 in the expansion chamber 36.

Eighth Embodiment

Figure 16:
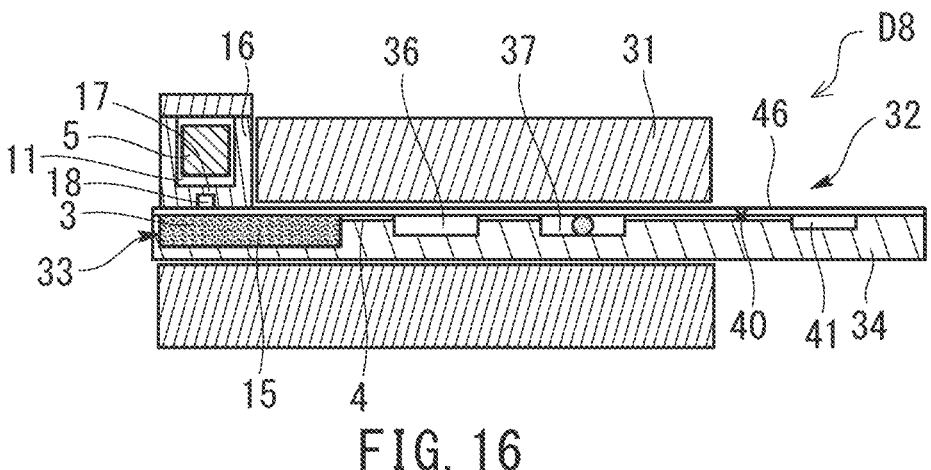
FIG. 16 illustrates a schematic sectional view of an eighth embodiment of a pyrotechnic cell disruption apparatus including a sample chip with downstream processing.
Figure 17:
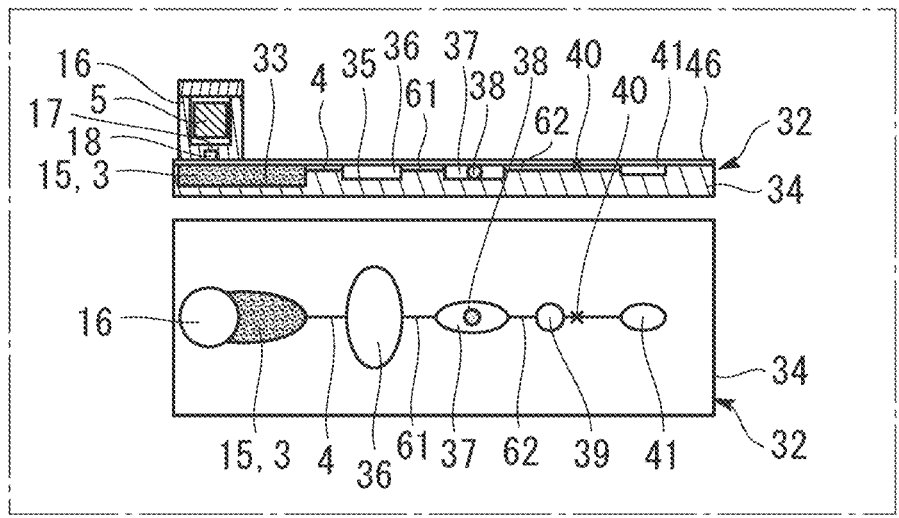
FIG. 17 illustrates a sectional view like FIG. 16 without clamps and a plan view in a first configuration prior to pressurizing.
Figure 18:
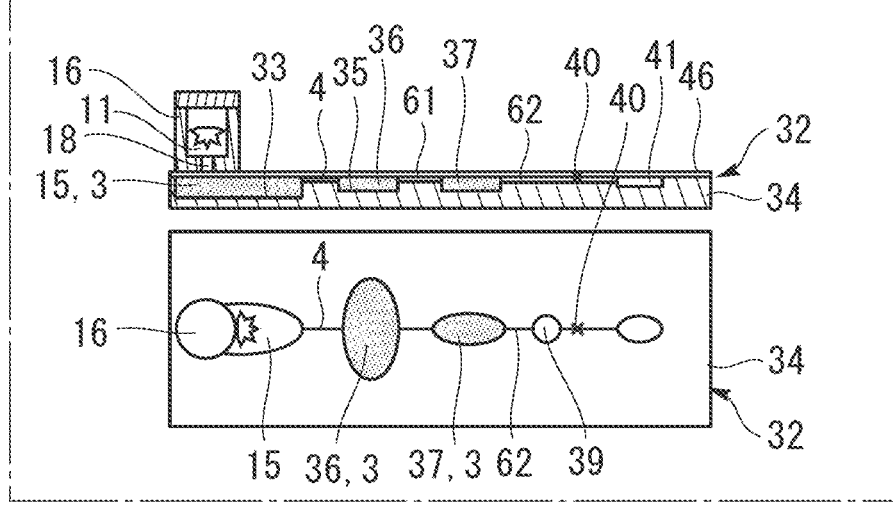
FIG. 18 illustrates a sectional view like FIG. 16 without clamps and a plan view in a second configuration after pressurizing.

FIGS. 16-18 demonstrate an eighth embodiment very similar to FIGS. 13-15 but in addition allowing for downstream processing of the disrupted cells on the chip. Similar elements are denoted by the same reference numerals as used in FIGS. 13-15. This eighth embodiment may for instance be applied as a Point of Care (POC) device. The first recess 33 in the substrate, as illustrated in FIG. 17, has a more elongated shape in this embodiment, while the expansion chamber 36 has an oval shape. Followed by the expansion chamber is a downstream reaction chamber 37 including a reagent 38, for instance for accomplishing polymerase chain reaction PCR. An optional air vent 39 may be provided, that could be configured to release pressure only partially so that a remainder of the pressure is maintained. This air vent 39 facilitates the filling of the chamber 37. It may be a hydrophobic vent such that once the chamber is filled, the vent hydrolocks in which hydrolocked state it ceases to act like a vent and any residual pressure behind the liquid is maintained. Finally, a valve 40 can be provided, that may be opened after the PCR reaction has been completed, allowing the processed sample to move into a detection chamber 41.

As described above, an eighth pyrotechnic cell disruption apparatus D8 (see FIGS. 16 to 18) according to an eighth embodiment is a modification example of the seventh pyrotechnic cell disruption apparatus D7 described in FIGS. 13 to 15. FIG. 16 illustrates a schematic sectional view of the eighth pyrotechnic cell disruption apparatus D8, FIG. 17 illustrates a sectional view without the clamps and a plan view in the first configuration before pressurizing (before ignition of the pyrotechnic charge 5), and FIG. 18 illustrates a sectional view without the clamps and a plan view in the second configuration after pressurizing (after the ignition of the pyrotechnic charge 5). In each of FIGS. 17 and 18, the sectional view and the plan view are illustrated in the upper part and the lower part, respectively. Also, the plan views illustrated at the lower parts in FIGS. 17 and 18 illustrate the upper surface of the substrate 34 through the top layer film 46 in a see-through manner. In the present embodiment, similar reference signs will be used for similar elements as compared with the aforementioned embodiments.

The chip 32 in the eighth pyrotechnic cell disruption apparatus D8 further includes the reaction chamber 37 formed in the form of a third recess on the upper surface side of the substrate 34 and the detection chamber 41 formed in the form of a fourth recess on the upper surface side of the substrate 34 in addition to the first recess 33 (pressure chamber 15), the second recess 35 (expansion chamber 36), and the precision orifice 4. The reaction chamber 37 is connected to the expansion chamber 36 through the second channel 61. Also, the detection chamber 41 is connected to the reaction chamber 37 through the third channel 62. As illustrated in FIG. 17, the downstream reaction chamber 37 is disposed in a later stage (downstream side) of the expansion chamber 36, and the detection chamber 41 is disposed on a yet later stage (downstream side) of the reaction chamber 37. The second channel 61 and the third channel 62 may be formed by grooves opening in the upper surface of the substrate 34, for example. Also, the top layer film 46 that seals the pressure chamber 15, the expansion chamber 36, the precision orifice 4, the reaction chamber 37, the detection chamber 41, the second channel 61 and the third channel 62 is caused to adhere to the upper surface of the substrate 34 on the chip 32. In the example illustrated in FIG. 17, the ventilation hole 39 that communicates with the third channel 62 and the valve 40 that is disposed on the later stage position than the ventilation hole 39 in the third channel 62 are provided in the upper surface of the chip 32. The ventilation hole 39 can be formed by a recess opening in the upper surface of the substrate 34 and an opening in the top layer film 46 formed at a position overlapping the recess, for example. The ventilation hole 39 can perform ventilation to the outside through the opening in the top layer film 46 and the clearance between the top layer film 46 and the clamps 31 and can introduce the atmospheric pressure to the expansion chamber 36, the reaction chamber 37, and the like by opening them to the atmosphere (outside). Also, when the valve 40 is opened, the atmospheric pressure is introduced to the detection chamber 41 as well through the ventilation hole 39.

According to the eighth pyrotechnic cell disruption apparatus D8 configured as described above, it is possible to successively move the fluid sample 3 to the reaction chamber 37 and the detection chamber 41 in the later stages after the fluid sample 3 in which the cells have been disrupted by the ignition and the combustion of the pyrotechnic charge 5 are collected in the expansion chamber 36. In the present embodiment, the ventilation hole 39 is provided in the chip 32, and it is thus possible to easily transfer the fluid sample 3 from the pressure chamber 15 to the expansion chamber 36 and the reaction chamber 37. Also, the reaction chamber 37 in the present embodiment receives the reagent 38 for causing a chemical reaction in the cells after disruption contained in the fluid sample 3. For example, the reagent 38 is a reagent for achieving a polymerase chain reaction PCR. By opening the valve 40 after the PCR reaction is completed in the reaction chamber 37, it is possible to transfer the fluid sample 3 containing the cells after reacting with the reagent 38 to the detection chamber 41 through the third channel 62. Note that in the present embodiment, the reagent 38 received in the downstream reaction chamber 37 is not limited to the reagent for achieving the polymerase chain reaction (PCR) and may be a reagent for carrying out loop-mediated iso-thermal amplification (LAMP) or any other isothermal amplification-related reactions, for example. Also, a plurality of types of reagents may be received in the reaction chamber 37.

Ninth Embodiment

Figure 19:
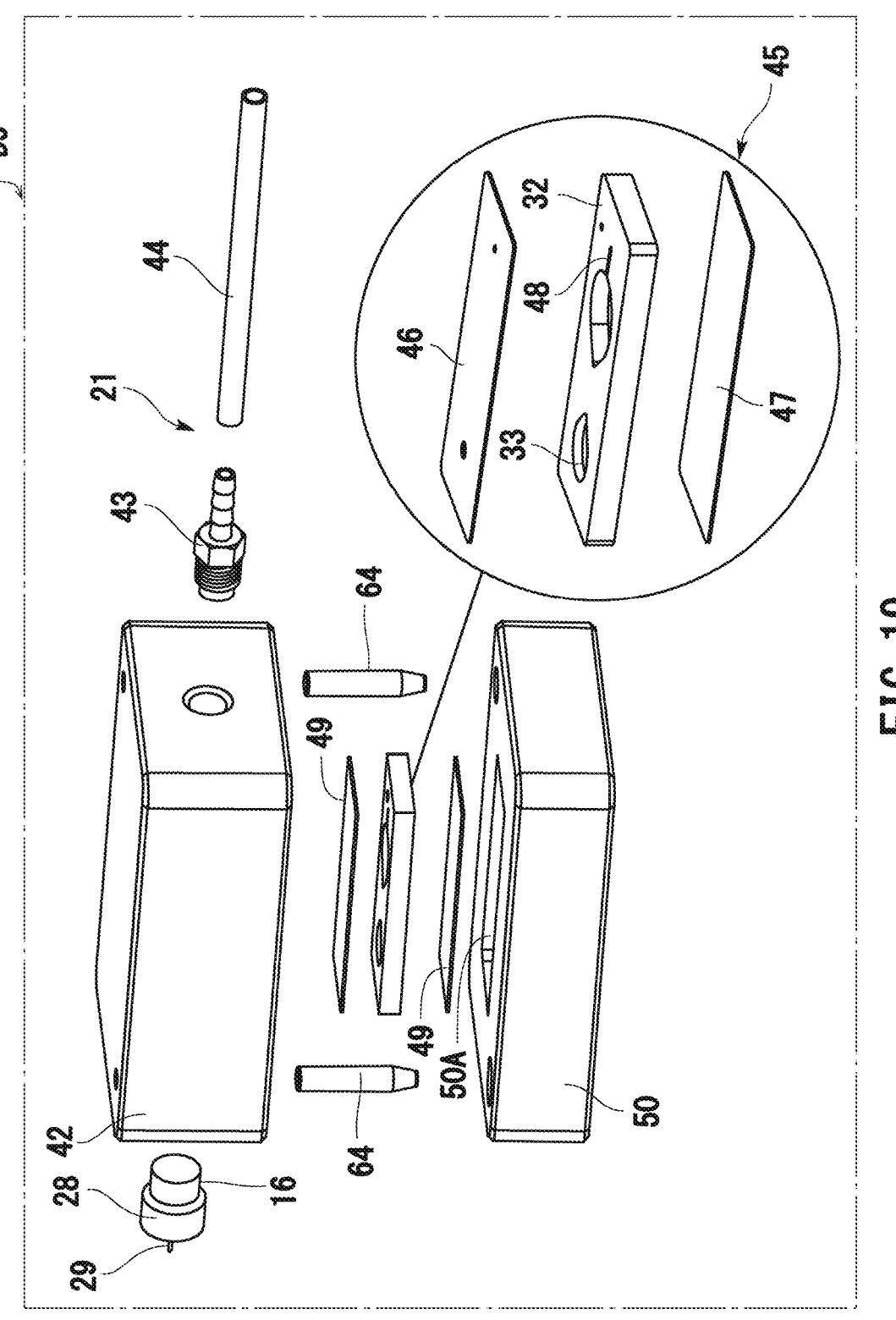
FIG. 19 illustrates an exploded view of a ninth embodiment of a pyrotechnic cell disruption apparatus.

FIG. 19 illustrates an exploded view of a ninth embodiment of a pyrotechnic cell disruption apparatus based on the concept illustrated in FIGS. 13-15, but illustrating more structural details. The clamp 31 is formed as a top housing 42, accommodating the initiator 28 on one end, and comprising a pressure relief 21 on its other end, including a threaded barb connector 43 and an ID tubing 44, for example ³⁄₁₆ inch in diameter. A chip assembly 45 includes the chip 32, a top layer film 46 and a bottom layer film 47, wherein the top layer film 46 and the bottom layer film 47 sandwiches the chip 32 and therefore seals it, including the sample provided in the first recess 33. Further, the chip assembly may be provided with a vent 48.

When mounted, the chip assembly 45 is sandwiched between the silicone gaskets 49, and the top housing 42, a bottom housing 50, and the gaskets 49. The chip assembly 45 may be moved together by locating pins provided in the holes in the top housing 42 and bottom housing 50 on diagonally opposing corners.

Figure 20:
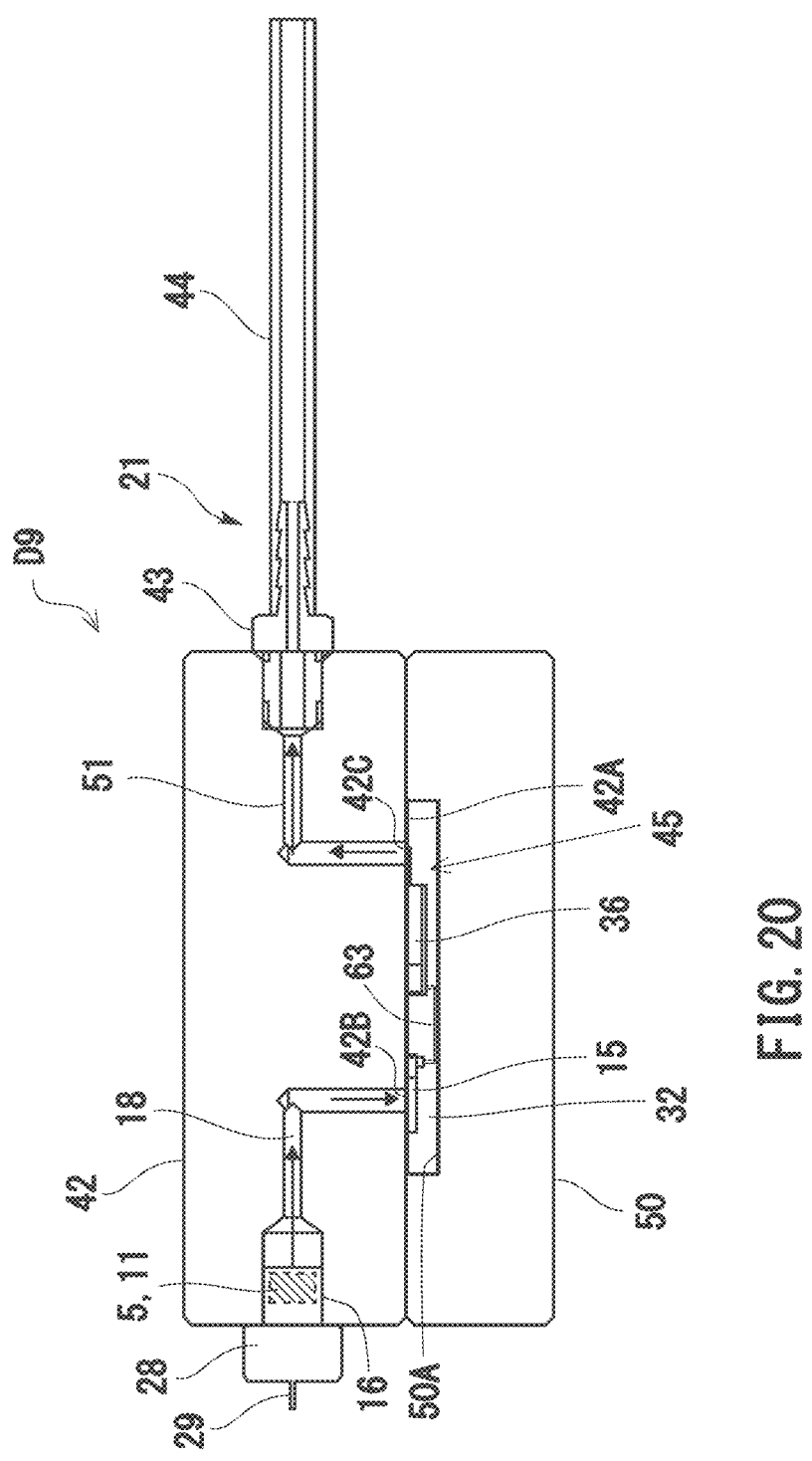
FIG. 20 illustrates a schematic sectional view of the ninth embodiment of a pyrotechnic cell disruption apparatus.

FIG. 20 illustrates a schematic sectional view of the ninth embodiment and illustrates the pressure release channel 18 as well as the venting channels 51 releasing the pressure after the pyrotechnic charge has combusted.

Figure 21:
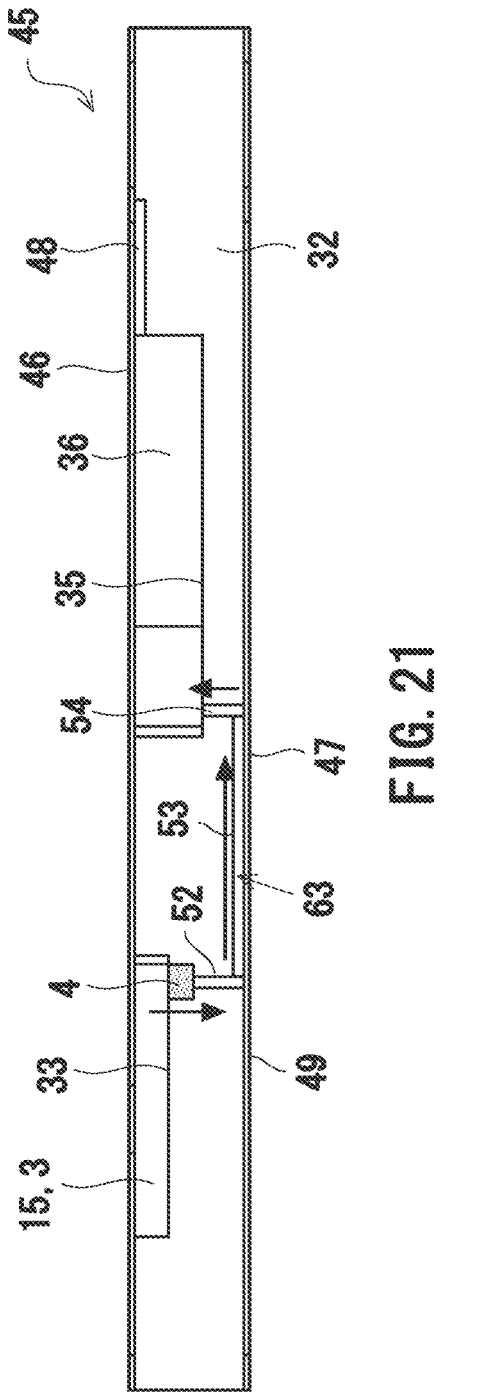
FIG. 21 illustrates a sectional view of the chip only illustrated in FIGS. 19 and 20 for demonstrating the cell disruption method in a first step.
Figure 22:
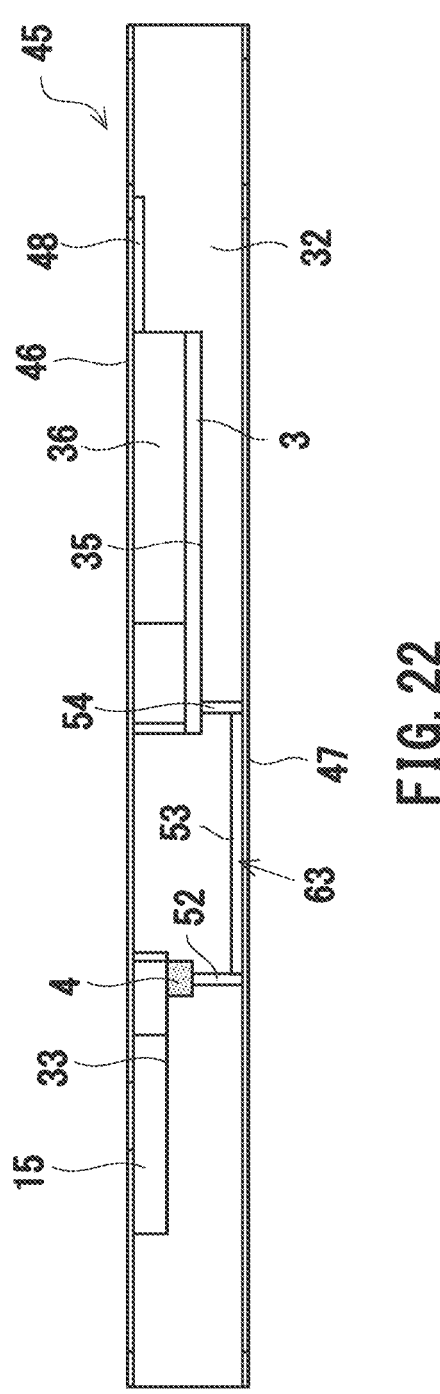
FIG. 22 illustrates a sectional view of the chip only illustrated in FIGS. 19 and 20 for demonstrating the cell disruption method in a second step.

As demonstrated in FIGS. 21 and 22, the sample is pushed down through a downward channel 52, moves along the precision orifice 4 in the form of a groove channel within in the chip 32 sealed by the gasket 49, and moves then through an upward channel 54 into the expansion chamber 36. In the alternative, it is possible to use a precision orifice not formed in the channel of the chip. Such an orifice could be made of sapphire or ruby or any other suitable material and be bonded or pressed into a recess of the chip. FIG. 22 illustrates the second configuration after combustion of the pyrotechnic charge, where the fluid sample 3 sits on the bottom of the expansion chamber 36, the sample now being processed to comprise disrupted cells with the cell content released for further processing by reagents and finally detection.

As described above, a pyrotechnic cell disruption apparatus D9 (see FIGS. 19 to 22) according to a ninth embodiment is achieved by specifying the seventh pyrotechnic cell disruption apparatus D7 with a more specific structure. In the present embodiment, similar reference signs will be used for similar elements as compared with the aforementioned embodiments. As illustrated in FIGS. 19 and 20, the ninth pyrotechnic cell disruption apparatus D9 includes: the chip 32 configured to include a substrate; the top layer film 46 that covers the upper surface of the chip 32; and the chip assembly 45 including the bottom layer film 47 that covers the lower surface of the chip 32. Note that FIGS. 21 and 22 are schematic sectional views of the chip assembly 45 in the ninth pyrotechnic cell disruption apparatus D9, in which FIG. 21 illustrates the first configuration before combustion of the pyrotechnic charge, and FIG. 22 illustrates the second configuration after combustion of the pyrotechnic charge.

In the chip 32 according to the ninth embodiment, the pressure chamber 15 is formed by the first recess 33 in the upper surface of the substrate, and the expansion chamber 36 is formed by the second recess 35 similarly to the seventh embodiment. As illustrated in FIG. 19, the chip 32 is provided with the ventilation hole 48 that communicates with the expansion chamber 36.

Also, as illustrated in FIGS. 21 and 22, the pressure chamber 15 and the expansion chamber 36 are connected via the first channel 63. The first channel 63 includes the precision orifice 4, the downward channel 52, the lateral channel 53, the upward channel 54, and the like. In the example illustrated in FIGS. 21 and 22, the upper end of the precision orifice 4 is connected to the bottom of the first recess 33 such that the pressure chamber 15 and the precision orifice 4 communicate, and the downward channel 52 connected to the lower end of the precision orifice 4 extends up to the lower surface of the chip 32. On the other hand, the upward channel 54 of the first channel 63 is provided such that the upper end is connected to the bottom of the second recess 35 forming the expansion chamber 36, the upward channel 54 extends downward from the bottom of the second recess 35, and the lower end thereof reaches the lower surface of the chip 32. The downward channel 52 and the upward channel 54 of the first channel 63 may be formed by a hole extending from the lower surface toward the upper surface side of the substrate 34, for example. Also, one end of the lateral channel 53 is connected to the lower end of the downward channel 52, and the other end is connected to the lower end of the upward channel 54. The lateral channel 53 may be formed by a groove channel opening in the lower surface of the chip 32, for example.

In the present embodiment, it is possible to seal the first recess 33 (pressure chamber 15) and the second recess 35 (expansion chamber 36) opening in the upper surface of the chip 32 from the outside by covering the upper surface of the chip 32 with the top layer film 46. Also, it is possible to seal the first channel 63 from the outside by covering the lower surface of the chip 32 with the bottom layer film 47.

As illustrated in FIGS. 19 and 20, the ninth pyrotechnic cell disruption apparatus D9 includes the pair of clamps 31 with rigidity formed in the housing form. In other words, the pair of clamps 31 include the top housing 42 as the upper clamp and the bottom housing 50 as the lower clamp. In the example illustrated in FIG. 19, the top housing 42 (upper clamp) and the bottom housing 50 (lower clamp) are formed as housings with substantially parallelepiped shapes. However, the shapes of the top housing 42 and the bottom housing 50 are not particularly limited. Here, a chip recess 50A capable of receiving the chip assembly 45 including the chip 32 is included on the upper surface side of the bottom housing 50 (lower clamp). Also, the lower surface of the top housing 42 (upper clamp) forms a clamp surface 42A that faces the loaded region of the chip 32 and is substantially flat. Also, each of facing corners on the diagonals in the top housing 42 and the bottom housing 50 is provided with a hole into which a coupling pin 64 is fitted.

As illustrated in FIGS. 19 and 20, the initiator 28 is attached to one side surface of the top housing 42 (upper clamp), and a screwed barb connector 43 of the pressure relief 21 is attached to the side surface on the opposite side. The initiator 28 includes the pyrotechnic charge chamber housing 16 that forms the pyrotechnic charge chamber 11, the pyrotechnic charge 5 that is received in the pyrotechnic charge chamber 11, a wire 29, and the like. The initiator is fixed to the top housing 42 such that the pyrotechnic charge chamber housing 16 is received inside the top housing 42 and the wire 29 is exposed to the outside. Also, one end of the pressure release channel 18 is connected to the pyrotechnic charge chamber housing 16 of the initiator 28. The pressure release channel 18 is formed by a conduit made of metal, for example, and the other end is joined to the clamp surface 42A of the top housing 42 from the inner side. Also, the opening portion on the side of the other end of the pressure release channel 18 communicates with the outside of the top housing 42 through a gas flow outlet 42B that is an opening formed in the clamp surface 42A. The pressure release channel 18 discharges the combustion gas of the pyrotechnic charge 5 from the gas flow outlet 42B in the clamp surface 42A of the top housing 42 upon operations of the initiator 28 by communicating with the pyrotechnic charge chamber 11 of the initiator 28 in advance or splitting due to combustion engine of the pyrotechnic charge 5, for example. Note that the opening end of the pressure release channel 18 and the gas flow outlet 42B in the clamp surface 42A may be located at the center of the first recess 33 (pressure chamber 15) on the chip 32.

As illustrated in FIG. 20, an ID tubing 44 and a ventilation channel 51 are connected to the screwed barb connector 43 of the pressure relief 21. The ID tubing 44 is a hollow pipe and is disposed outside the top housing 42. Also, the ventilation channel 51 is formed of a conduit made of metal, for example. One end of the ventilation channel 51 is connected to the screwed barb connector 43, and the other end is joined to the clamp surface 42A of the top housing 42 from the inner side. Also, the opening portion on the side of the other end of the ventilation channel 51 communicates with the outside of the top housing 42 through the ventilation hole 42C that is an opening formed in the clamp surface 42A. Note that the inside of the screwed barb connector 43 is hollow, and ventilation pathways are formed inside the ventilation channel 51, the screwed barb connector 43, and the ID tubing 44.

When the ninth pyrotechnic cell disruption apparatus D9 configured as described above is assembled, the chip assembly 45 is received in the chip recess 50A of the bottom housing 50. At that time, the chip assembly 45 is received in the chip recess 50A in a state in which it is sandwiched between the pair of gaskets 49 as illustrated in FIG. 19. It is possible to assemble the ninth pyrotechnic cell disruption apparatus D9 by receiving the chip assembly 45 sandwiched between the pair of gaskets 49 in this manner in the chip recess 50A and then integrally fixing the top housing 42 and the bottom housing 50 using the coupling pins 64. However, the coupling structure for the top housing 42 and the bottom housing 50 is not particularly limited.

Once the initiator 28 of the ninth pyrotechnic cell disruption apparatus D9 operates, the pyrotechnic charge 5 is ignited and combusts, and the combustion gas is discharged from the gas flow outlet 42B formed in the clamp surface 42A of the top housing 42 through the pyrotechnic charge chamber 11 and the pressure release channel 18. Here, opening portions for ventilating the combustion gas discharged from the gas flow outlet 42B to the pressure chamber 15 on the chip 32 are formed in the top layer film 46 of the chip assembly 45 and the gasket 49 disposed on the side of the upper surface of the chip assembly 45. In this manner, the combustion gas from the pressure release channel 18 flows into the pressure chamber 15, the pressure chamber 15 is thus suddenly pressurized, and the cells contained in the fluid sample 3 received in the pressure chamber 15 are disrupted.

Also, the fluid sample 3 pressurized in the pressure chamber 15 successively passes through the precision orifice 4 of the first channel 63, the downward channel 52, the lateral channel 53, and the upward channel 54 and is then transferred to the expansion chamber 36. When the fluid sample 3 flows through the precision orifice 4, the cells contained in the fluid sample 3 receive large shear stress, and disruption of the cells is thus promoted. Here, the openings are formed in the top layer film 46 of the chip assembly 45 and the gasket 49 disposed on the side of the upper surface of the chip assembly 45 at positions overlapping the ventilation hole 48, and the ventilation hole 42C formed in the clamp surface 42A of the top housing 42 is also disposed at the position overlapping the ventilation hole 48. In this manner, ventilation to the expansion chamber 36 of the chip assembly 45 is established through the ventilation hole 48 and the pressure relief 21 (the ventilation channel 51, the screwed barb connector 43, and the ID tubing 44), and the atmospheric pressure is introduced therein. Therefore, the fluid sample 3 that has been transferred from the pressure chamber 15 to the expansion chamber 36 through the first channel 63 is decompressed in the expansion chamber 36. As a result, the cells contained in the fluid sample 3 suddenly expand, and it is thus possible to further promote disruption of the cells. As described above, the fluid sample 3 after the cells are subjected to the disruption processing are collected in the expansion chamber 36 in the chip assembly 45 (chip 32).

It is a matter of course that the top housing 42 and the bottom housing 50 are detachable in the present embodiment. After operations (after use) of the ninth pyrotechnic cell disruption apparatus D9, the top housing 42 and the bottom housing 50 are separated by detaching the coupling pins 64 or the like, and the chip assembly 45 (chip 32) received in the chip recess 50A of the bottom housing 50 is exposed. Thereafter, the top layer film 46 covering the upper surface of the chip 32 is removed by peeling, for example, and it is thus possible to collect the fluid sample 3 after the cell disruption processing from the expansion chamber 36. In the present embodiment, a reagent may be added to the fluid sample 3 collected in the expansion chamber 36 to carryout various kinds of reaction processing as described in the seventh embodiment.

Tenth Embodiment

FIGS. 23-26 illustrate an embodiment very similar to FIGS. 19-22. However, the chip is substituted by a laser cut plastic chip with the precision orifice created in the chip geometry. Consequently, the chip is essentially an integrated part of the bottom housing 50. This embodiment does not include a designated venting, but venting happens through the gap between the top housing 42 and the bottom housing 50.

Figure 23:
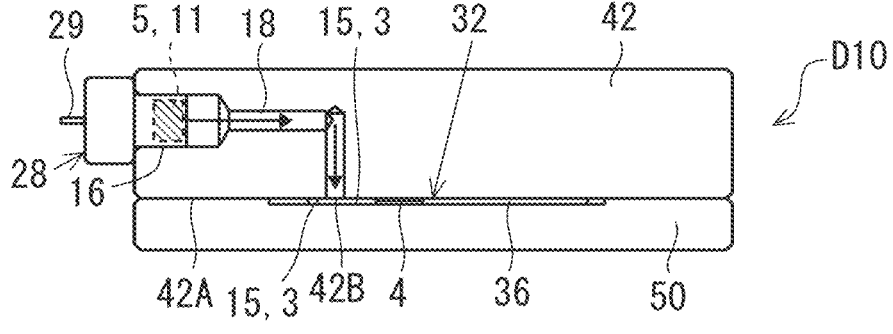
FIG. 23 illustrates a sectional view of a tenth embodiment similar to FIGS. 19-22, but having the chip being an integrated part of the lower housing.
Figure 24:
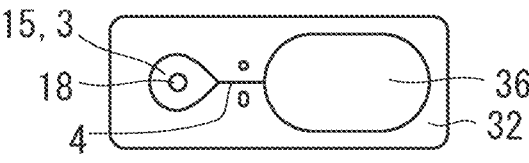
FIG. 24 illustrates a plan view of the tenth embodiment according to FIG. 23 of the lower housing part forming the chip.
Figures 25, 26:
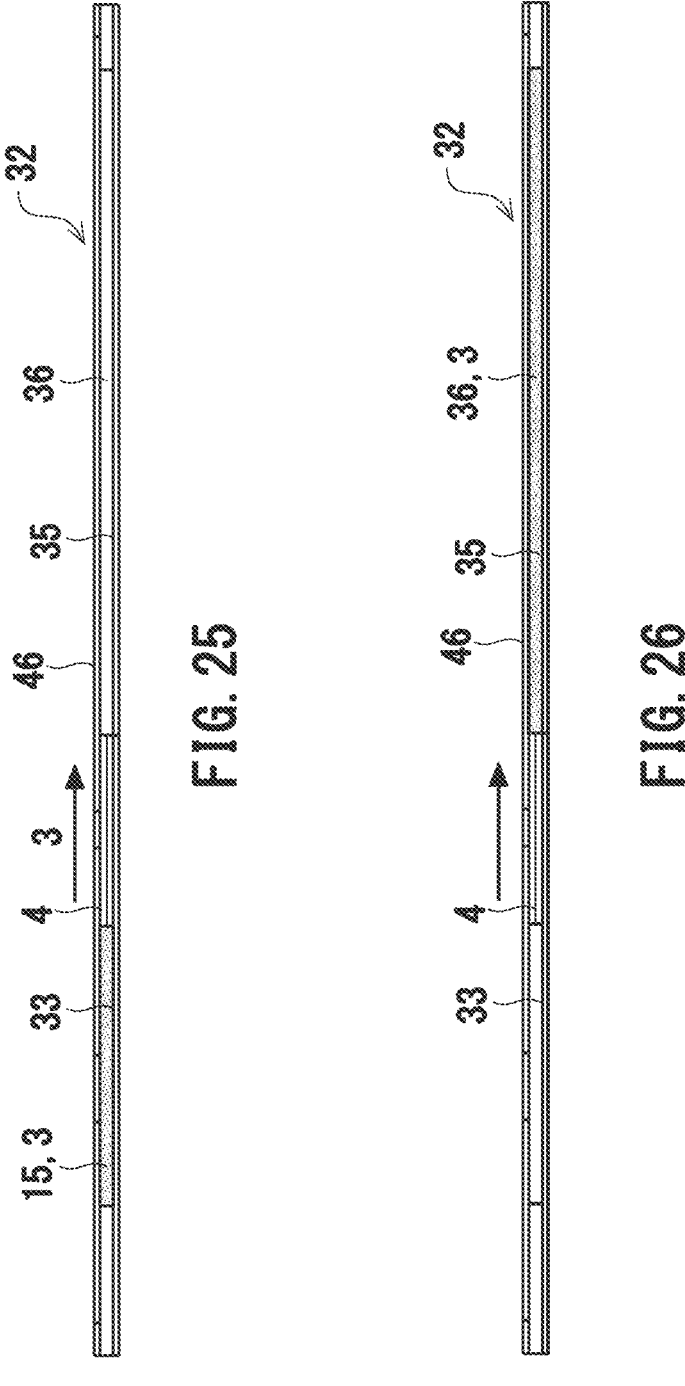
FIG. 25 illustrates a sectional view of the chip only for demonstrating the cell disruption method in a first step.
FIG. 26 illustrates a sectional view of the chip only for demonstrating the cell disruption method in a second step.

FIG. 23 illustrates a sectional view of a tenth pyrotechnic cell disruption apparatus D10 according to a tenth embodiment. The tenth pyrotechnic cell disruption apparatus D10 is a modification example of the ninth pyrotechnic cell disruption apparatus D9. In the present embodiment, similar reference signs will be used for similar elements as compared with the aforementioned embodiments. In the tenth pyrotechnic cell disruption apparatus D10, the chip 32 is formed into a chip shape by working the upper surface of the bottom housing 50 using a laser cut technique, and the tenth pyrotechnic cell disruption apparatus D10 is realized in the form in which the chip 32 is integrated with the bottom housing 50. FIG. 24 is a plan view of a chip formation region where the chip 32 is formed in the upper surface of the bottom housing 50. The chip formation region in the bottom housing 50 can be formed by a polymer material (such as plastic) or glass, for example. Also, FIGS. 25 and 26 are schematic sectional views of the chip 32 (the chip formation region in the bottom housing 50) in the tenth pyrotechnic cell disruption apparatus D10, in which FIG. 25 illustrates the first configuration before combustion of the pyrotechnic attachment, and FIG. 26 illustrates the second configuration after combustion of the pyrotechnic attachment.

The chip 32 formed by being integrated with the chip formation region in the bottom housing 50 is provided with the pressure chamber 15 that is formed by the first recess 33 and is capable of receiving the fluid sample 3 before the cell disruption processing and the expansion chamber 36 that is formed by the second recess 35, and the pressure chamber 15 and the expansion chamber 36 are connected via the first channel 63 including the precision orifice 4. Similarly to the seventh embodiment, the expansion chamber 36 on the chip 32 has a sufficiently large volume as compared with the pressure chamber 15, such that the fluid sample 3 is decompressed and the cells contained in the fluid sample 3 suddenly expand when the fluid sample 3 enters the expansion chamber 36 from the pressure chamber 15.

The top housing 42 in the tenth pyrotechnic cell disruption apparatus D10 is provided with the initiator 28 and the pressure release channel 18 similarly to the ninth embodiment, while it is not provided with the pressure relief 21. Similarly to the ninth embodiment, each of the top housing 42 and the bottom housing 50 is provided with a hole into which the coupling pin is fitted, and it is possible to integrally couple the top housing 42 and the bottom housing 50 using the pins and to separate the top housing 42 and the bottom housing 50 after the operations of the apparatus. Also, the upper surface of the chip 32 integrated with the bottom housing 50 may be covered with the top layer film 46. In this case, a small hole for ventilation of the combustion gas discharged from the gas flow outlet 42B in the clamp surface 42A of the top housing 42 to the pressure chamber 15 or a vulnerable portion may be formed in the top layer film 46. When the top housing 42 is assembled with the bottom housing 50, a gasket 49 may be interposed between the upper surface of the chip 32 integrated with the bottom housing 50 and the clamp surface 42A of the top housing 42, and in this case, an opening portion may be formed in the gasket 49, and the combustion gas discharged from the gas flow outlet 42B in the clamp surface 42A may be supplied to the pressure chamber 15.

Operations of the tenth pyrotechnic cell disruption apparatus D10 configured as described above are basically similar to those of the ninth pyrotechnic cell disruption apparatus D9 in the ninth embodiment. In other words, once the initiator 28 operates, the pyrotechnic charge 5 is ignited and combusts, the combustion gas is supplied to the pressure chamber 15 on the chip 32 through the pressure release channel 18, the fluid sample 3 received in the pressure chamber 15 is thus suddenly pressurized, and the cells contained in the fluid sample 3 are disrupted. Then, the fluid sample 3 pressurized in the pressure chamber 15 is transferred to the expansion chamber 36 through the first channel 63 including the precision orifice 4. When the fluid sample 3 flows through the precision orifice 4, the cells contained in the fluid sample 3 receive large shear stress, and disruption of the cells is thus promoted. Once the fluid sample 3 flows into the expansion chamber 36 with a large volume from the first channel 63, the cells contained in the fluid sample 3 are decompressed and suddenly expand, and cell disruption is further promoted. In this manner, the fluid sample 3 containing the cells after the disruption processing are collected in the expansion chamber 36. Note that the chip 32 may be provided with the ventilation hole 48 that communicates with the expansion chamber 36, and the atmospheric pressure may be introduced into the expansion chamber 36 via the ventilation hole 48, similarly to the ninth embodiment.

Eleventh Embodiment

Figure 29:
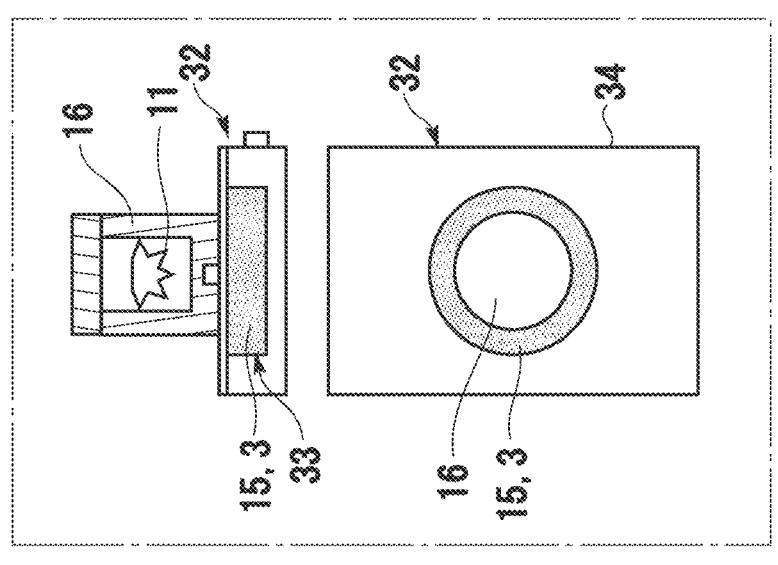
FIG. 29 illustrates a sectional view like FIG. 27 without clamps and a plan view in a second configuration after pressurizing.
Figure 29:
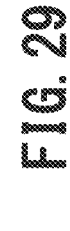
Figure 28:
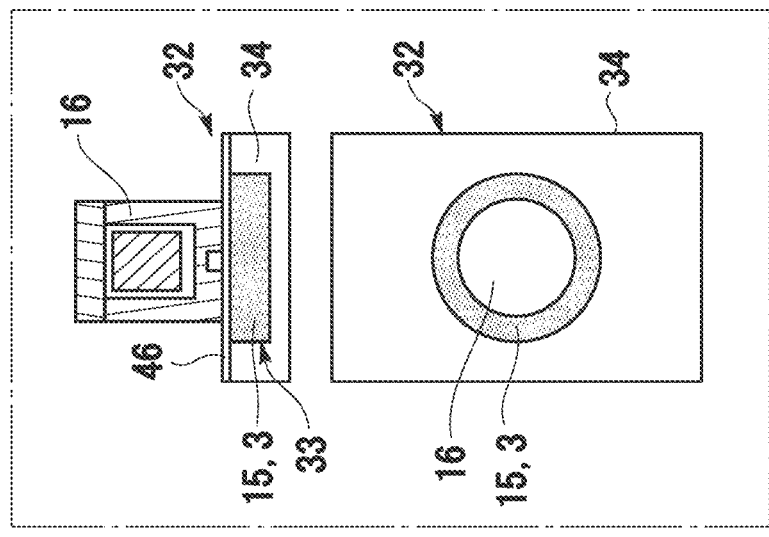
FIG. 28 illustrates a sectional view like FIG. 27 without clamps and a plan view in a first configuration prior to pressurizing.
Figure 27:
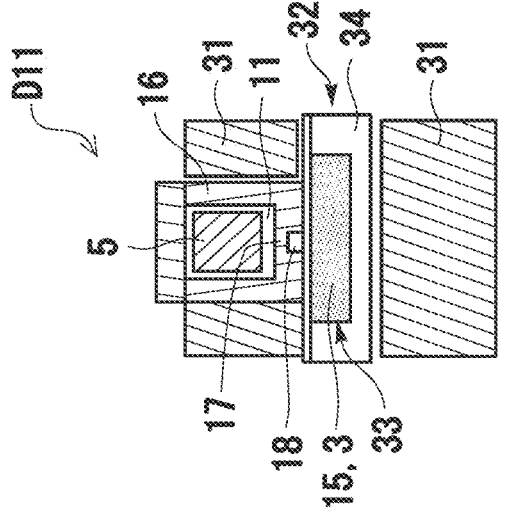
FIG. 27 illustrates a schematic sectional view of an eleventh embodiment of a pyrotechnic cell disruption apparatus including a sample chip.

FIGS. 27-29 illustrate a schematic sectional view of an eleventh embodiment of a pyrotechnic cell disruption apparatus including a sample chip, with FIG. 28 schematically demonstrating the chip in a first configuration prior to pressurizing and FIG. 29 in a second configuration after pressurizing. This embodiment is similar to the embodiment illustrated in FIGS. 13-15, but does not include any orifice 4. Therefore, this embodiment is based on the same hydrostatic shock pressure wave concept as the embodiment discussed in FIGS. 5 and 6. Similar elements as described in FIGS. 13-15 are denoted by the same reference numerals.

This eleventh embodiment according to FIGS. 27-29 essentially takes the concept of the third embodiment according to FIGS. 5 and 6 to a chip format. Although only one single recess 33 is holding the fluid sample 3, also chips having several recesses 33 for several different samples are possible on one single chip. Several pyrotechnic charges 5 can be applied simultaneously on a multiple-sample chip, or a single pyrotechnic charge housing can be moved from sample to sample, being recharged while moved between samples.

An eleventh pyrotechnic cell disruption apparatus D11 illustrated in FIGS. 27 to 29 includes the chip 32 (pyrotechnic cell destruction chip) including the substrate 34 and the pressure chamber 15 formed by the first recess 33 formed in the substrate 34. Moreover, the eleventh pyrotechnic cell disruption apparatus D11 includes the pair of clamps 31 that clamp the chip 32 by being disposed at the upper portion (top) and the lower portion (bottom) of the chip 32 (the pyrotechnic cell destruction chip), the pyrotechnic charge chamber housing 16 that forms the pyrotechnic charge chamber 11, the pyrotechnic charge 5 that is received in the pyrotechnic charge chamber 11, and the like. Also, the chip 32 includes toe thin top layer film 46 that covers the upper surface of the substrate 34, and it is possible to tightly close the first recess 33 (pressure chamber 15) in the substrate 34 from the outside with the top layer film 46. Note that FIG. 28 schematically illustrates a sectional view and a plan view of the eleventh pyrotechnic cell disruption apparatus D11 before operations (before pressurizing). In FIG. 28, illustration of the clamps 31 is omitted, and the sectional view and the plan view are illustrated in the upper part and the lower part, respectively. FIG. 29 schematically illustrates a sectional view and a plan view of the eleventh pyrotechnic cell disruption apparatus D11 after operations (after pressurizing). In FIG. 29, illustration of the clamps 31 is omitted, and the sectional view and the plan view are illustrated in the upper part and the lower part, respectively. Note that in the plan views of FIGS. 28 and 29, the upper surface of the substrate 34 is illustrated through the top layer film 46 in a see-through manner.

Once the eleventh pyrotechnic cell disruption apparatus D11 configured as described above operates, the pyrotechnic charge 5 is ignited, the pyrotechnic charge 5 combusts, and combustion gas is thus generated. In this manner, the pressure in the pyrotechnic charge chamber 11 rises, the breaking point 17 of the pyrotechnic charge chamber housing 16 ruptures, and the pressure release channel 18 communicates with the pyrotechnic charge chamber 11. As a result, the pressure in the pyrotechnic charge chamber 11 is released, the portion of the top layer film 46 facing the pressure release channel 18 breaks, and the combustion gas flows into the pressure chamber 15 on the chip 32. Alternatively, a small hole may be formed in advance at a portion of the top layer film 46 facing the pressure release channel 18, and the combustion gas may be supplied to the pressure chamber 15 through the small hole. The pressure chamber 15 to which the combustion gas of the pyrotechnic charge 5 has been supplied is quickly pressurized, and as a result, it is possible to disrupt the cells contained in the fluid sample 3 received in the pressure chamber 15. Also, the eleventh pyrotechnic cell disruption apparatus D11 may include the precision orifice 4 and the pressure relief 21 described in the aforementioned embodiments.

In regard to the above embodiments, the following supplementary notes will be further described.

Supplementary Note 1

A pyrotechnic cell disruption apparatus including:
a pyrotechnic charge configured to be ignited and to combust upon ignition; and
a pressure chamber configured to receive a fluid sample containing cells and to be pressurized upon ignition and combustion of the pyrotechnic charge.

Supplementary Note 2

The pyrotechnic cell disruption apparatus according to Supplementary note 1, further including:
a pressure chamber outlet that connects the pressure chamber to an exterior space,
in which the pressure chamber outlet includes an orifice that causes shear stress to act on the fluid sample when the fluid sample is distributed.

Supplementary Note 3

The pyrotechnic cell disruption apparatus according to Supplementary note 2, in which the orifice is formed at a separated portion that is caused to adhere or pressure-fitted to the pressure chamber outlet.

Supplementary Note 4

The pyrotechnic cell disruption apparatus according to any one of Supplementary notes 1 to 3, in which the pyrotechnic charge is received in another pyrotechnic charge chamber that is separated from the pressure chamber.

Supplementary Note 5

The pyrotechnic cell disruption apparatus according to Supplementary note 4, in which the pyrotechnic charge chamber is formed in a pyrotechnic charge chamber housing that includes a breaking point that ruptures upon the ignition and the combustion of the pyrotechnic charge.

Supplementary Note 6

The pyrotechnic cell disruption apparatus according to Supplementary note 5, in which the breaking point is formed by a vulnerable portion of the pyrotechnic charge chamber housing that faces the pressure chamber and is more vulnerable than the other portions.

Supplementary Note 7

The pyrotechnic cell disruption apparatus according to Supplementary note 6, in which at the vulnerable portion, a member thickness of the pyrotechnic charge chamber housing is formed to be thinner than the other portions.

Supplementary Note 8

The pyrotechnic cell disruption apparatus according to any one of Supplementary notes 5 to 7, in which the pyrotechnic charge chamber opens directly to the pressure chamber upon breaking of the breaking point.

Supplementary Note 9

The pyrotechnic cell disruption apparatus according to any one of Supplementary notes 1 to 3, further including:

a first cylinder chamber that receives the pyrotechnic charge;

a first piston that has at least a part received in the first cylinder chamber and is movable relative to the first cylinder chamber under a pressure generated by the ignition and the combustion of the pyrotechnic charge; and a second piston that is provided inside the pressure chamber and is connected to the first piston, in which the fluid sample received in the pressure chamber is pressurized by the second piston working in conjunction with the first piston upon the ignition and the combustion of the pyrotechnic charge.

Supplementary Note 10

The pyrotechnic cell disruption apparatus according to Supplementary note 9, in which the first cylinder chamber is formed in a first cylinder chamber housing that includes at least a part received in the pressure chamber.

Supplementary Note 11

The pyrotechnic cell disruption apparatus according to any one of Supplementary notes 1 to 8, further including:

a diaphragm that sections the pressure chamber into a first interior space into which combustion gas of the pyrotechnic charge is introduced upon the ignition and the combustion of the pyrotechnic charge and a second interior space that receives the fluid sample, in which the diaphragm is deformed by the combustion gas being introduced into the first interior space upon the ignition and the combustion of the pyrotechnic charge, and the fluid sample received in the second interior space is pressurized by a volume of the second interior space being reduced.

Supplementary Note 12

The pyrotechnic cell disruption apparatus according to Supplementary note 11, further including:

a pressure chamber outlet that connects the second interior space to an exterior space, in which the pressure chamber outlet includes an orifice that causes shear stress to act on the fluid sample when the fluid sample is distributed.

Supplementary Note 13

The pyrotechnic cell disruption apparatus according to any one of Supplementary notes 1 to 12, further including:

a pressure relief that relieves a pressure from the pressure chamber after the pressure chamber is pressurized by the ignition and the combustion of the pyrotechnic charge.

Supplementary Note 14

The pyrotechnic cell disruption apparatus according to Supplementary note 13, in which the pressure relief includes a valve body.

Supplementary Note 15

The pyrotechnic cell disruption apparatus according to Supplementary note 14, in which the valve body is a pressure release valve that is opened under a predetermined pressure.

Supplementary Note 16

The pyrotechnic cell disruption apparatus according to Supplementary note 13, in which the pressure relief includes a rupture plate that ruptures under a predetermined pressure.

Supplementary Note 17

The pyrotechnic cell disruption apparatus according to any one of Supplementary notes 13 to 16, in which a sample container that is filled with the fluid sample is received in the pressure chamber.

Supplementary Note 18

The pyrotechnic cell disruption apparatus according to Supplementary note 17, in which the sample container is a flexible pouch.

Supplementary Note 19

The pyrotechnic cell disruption apparatus according to Supplementary note 17 or 18, in which the pressure chamber includes a pressure channel where the pyrotechnic charge is disposed and a sample container receiving unit that is coaxially connected to the pressure channel and receives the sample container.

Supplementary Note 20

The pyrotechnic cell disruption apparatus according to Supplementary note 19, in which a sample container placing unit where the sample container is placed is formed at a portion of the sample container receiving unit connected to the pressure channel.

Supplementary Note 21

The pyrotechnic cell disruption apparatus according to Supplementary note 20, in which a cross-sectional area of the sample container receiving unit is larger than a cross-sectional area of the pressure channel, and the sample container placing unit is formed by a level difference formed between the sample container receiving unit and the pressure channel.

Supplementary Note 22

The pyrotechnic cell disruption apparatus according to any one of Supplementary notes 19 to 21, including:

a pressure container, inside which the pressure chamber is formed, with the sample container receiving unit opening to an upper surface; and a cap, in which the pressure relief is installed, which is able to be attached to the pressure container to cover an upper surface of the pressure container, in which the pressure relief includes a pressure relief vent pathway that causes the sample container receiving unit and an exterior space to communicate after the pressure chamber is pressurized by the ignition and the combustion of the pyrotechnic charge.

Supplementary Note 23

The pyrotechnic cell disruption apparatus according to Supplementary note 22, in which in a state where the cap is attached to the pressure container, the pressure channel, the sample container receiving unit, and the pressure relief vent pathway are coaxially disposed.

Supplementary Note 24

The pyrotechnic cell disruption apparatus according to Supplementary note 22 or 23, in which the pressure relief vent pathway is blocked by a rupture plate or a valve body, and the sample container receiving unit and an exterior space communicates by the rupture plate rupturing or the valve body being opened.

Supplementary Note 25

The pyrotechnic cell disruption apparatus according to Supplementary note 17 or 18,
  in which the pressure chamber includes a pressurized space unit that extends in a first direction and includes a proximal end and a distal end relative to the pressure relief and a pressure channel that branches from a midpoint of the pressurized space unit in a second direction different from the first direction and is connected to the pressurized space unit,
  the pyrotechnic charge is disposed in the pressure channel, and
  the pressurized space unit includes a sample container receiving unit that receives the sample container between the portion connected to the pressure channel and the distal end.

Supplementary Note 26

The pyrotechnic cell disruption apparatus according to Supplementary note 25, in which the first direction and the second direction perpendicularly intersect each other.

Supplementary Note 27

The pyrotechnic cell disruption apparatus according to Supplementary note 25 or 26, including:
  a pressure container with a bottomed shape, inside which the pressure chamber is formed, with a proximal end of the pressurized space unit opening to an upper surface; and
  a cap, in which the pressure relief is installed, which is able to be attached to the pressure container to cover an upper surface of the pressure container,
  in which the sample container is able to be placed on a bottom of the pressure container by the pressurized space unit extending in an up-down direction of the pressure container and by the distal end positioned at the bottom.

Supplementary Note 28

The pyrotechnic cell disruption apparatus according to any one of Supplementary notes 25 to 27,
  in which the pressure relief includes a pressure relief vent pathway that causes the pressurized space unit and an exterior space to communicate after the pressure chamber is pressurized by the ignition and the combustion of the pyrotechnic charge, and
  the proximal end of the pressurized space unit is connected to the pressure relief vent pathway.

Supplementary Note 29

The pyrotechnic cell disruption apparatus according to Supplementary note 28, in which in a state where the cap is attached to the pressure container, the pressurized space unit and the pressure relief vent pathway are coaxially disposed.

Supplementary Note 30

The pyrotechnic cell disruption apparatus according to Supplementary note 28 or 29, in which the pressure relief vent pathway is blocked by a rupture plate or a valve body, and the sample container receiving unit and an exterior space communicate by the rupture plate rupturing or the valve body being opened.

Supplementary Note 31

The pyrotechnic cell disruption apparatus according to Supplementary note 1, including:
  a chip that includes a substrate,
  in which the pressure chamber is formed by a first recess provided in a surface of the substrate.

Supplementary Note 32

The pyrotechnic cell disruption apparatus according to Supplementary note 31, including:
  a film that covers the surface of the substrate,
  in which the pressure chamber is tightly closed by the first recess being covered with the film.

Supplementary Note 33

The pyrotechnic cell disruption apparatus according to Supplementary note 31, further comprising:
  a pyrotechnic charge chamber housing that receives the pyrotechnic charge,
  in which the pyrotechnic charge chamber housing is disposed at an upper portion of the pressure chamber.

Supplementary Note 34

The pyrotechnic cell disruption apparatus according to Supplementary note 33,
  in which the pyrotechnic charge chamber housing includes a breaking point that ruptures upon the ignition and the combustion of the pyrotechnic charge, and
  the breaking point is disposed to face the pressure chamber.

Supplementary Note 35

The pyrotechnic cell disruption apparatus according to any one of Supplementary notes 31 to 34, further including:
  an expansion chamber that is formed by a second recess provided in the surface of the substrate; and
  a first channel that is provided in the substrate and connects the pressure chamber and the expansion chamber, in which the first channel includes an orifice that causes shear stress to act on the fluid sample when the fluid sample is distributed.

Supplementary Note 36

The pyrotechnic cell disruption apparatus according to Supplementary note 35, in which the expansion chamber has a larger volume than the pressure chamber, and the fluid sample is decompressed when the fluid sample flows from the pressure chamber into the expansion chamber through the orifice.

Supplementary Note 37

The pyrotechnic cell disruption apparatus according to Supplementary note 35 or 36, in which the expansion chamber is opened to outside.

Supplementary Note 38

The pyrotechnic cell disruption apparatus according to any one of Supplementary notes 35 to 37, further including:
a reaction chamber that is formed by a third recess provided in the surface of the substrate and receives a reagent that causes the cells contained in the fluid sample to react; and
a second channel that is provided in the substrate and connects the expansion chamber and the reaction chamber.

Supplementary Note 39

The pyrotechnic cell disruption apparatus according to Supplementary note 38, in which the reaction chamber is opened to outside.

Supplementary Note 40

The pyrotechnic cell disruption apparatus according to Supplementary note 38 or 39, further including:
a detection chamber that is formed by a fourth recess provided in the surface of the substrate; and
a third channel that is provided in the substrate and connects the reaction chamber and the detection chamber.

Supplementary Note 41

The pyrotechnic cell disruption apparatus according to any one of Supplementary notes 31 to 40, further including:
a pair of clamps that clamp the chip.

Supplementary Note 42

The pyrotechnic cell disruption apparatus according to Supplementary note 41, in which the pair of clamps include an upper clamp that includes a substantially flat clamp surface that faces a loaded region of the chip and a lower clamp that includes a chip recess configured to receive the chip.

Supplementary Note 43

The pyrotechnic cell disruption apparatus according to Supplementary note 42, in which each of the upper clamp and the lower clamp has a housing form.

Supplementary Note 44

A pyrotechnic cell disruption method including:
receiving a fluid sample containing cells in a pressure chamber configured to be pressurized by a pyrotechnic charge; and
pressurizing the fluid sample received in the pressure chamber by igniting and combusting the pyrotechnic charge.

Supplementary Note 45

The pyrotechnic cell disruption method according to Supplementary note 44, further including:
holding a pressure inside the pressure chamber generated by the combustion of the pyrotechnic charge for a certain period.

Supplementary Note 46

The pyrotechnic cell disruption method according to Supplementary note 44 or 45, further including:
discharging the fluid sample pressurized in the pressure chamber to an exterior space through an orifice,
in which shear force generated upon passing through the orifice is caused to act on the fluid sample.

Supplementary Note 47

The pyrotechnic cell disruption method according to Supplementary note 46, in which the exterior space is an expansion chamber that receives the fluid sample that has passed through the orifice, and the fluid sample is expanded when the fluid sample is received in the expansion chamber.

Supplementary Note 48

The pyrotechnic cell disruption method according to Supplementary note 47, further including:
adding a reagent to the fluid sample inside the expansion chamber to cause the fluid sample to react with the reagent.

Supplementary Note 49

The pyrotechnic cell disruption method according to Supplementary note 47, further including:
causing the fluid sample to move from the expansion chamber into the reaction chamber with a reagent received therein to cause the fluid sample to react with the reagent inside the reaction chamber.

Supplementary Note 50

The pyrotechnic cell disruption method according to Supplementary note 49, further including:
causing the fluid sample to react with the reagent inside the reaction chamber and then discharging the fluid sample from the reaction chamber into the detection chamber.

Supplementary Note 51

The pyrotechnic cell disruption method according to any one of Supplementary notes 48 to 50, in which a reaction caused by the reagent is a polymerase chain reaction (PCR) or loop-mediated isothermal amplification (LAMP).

Supplementary Note 52

The pyrotechnic cell disruption method according to any one of Supplementary notes 44 to 51, in which the pyrotechnic cell disruption method does not include lysing of cells contained in the fluid sample using a chemical substance.

Each configuration disclosed in the present specification can also be combined with any other features disclosed in the present specification.

REFERENCE SIGNS LIST

D1-D11 Pyrotechnic cell disruption apparatus
1 Cylinder body
2 Piston
3 Sample
4 Precision orifice
5 Pyrotechnic charge
6 Cap
7 Low-pressure space
8 High-pressure space
11 Pyrotechnic charge chamber
14 Diaphragm
15 Pressure chamber
16 Pyrotechnic charge chamber housing
20 Pressure release valve
28 Initiator
31 Clamp
32 Chip
33 First recess
34 Substrate
35 Second recess
36 Expansion chamber
37 Reaction chamber
38 Reagent
41 Detection chamber

The invention claimed is:

1. A pyrotechnic cell disruption apparatus comprising:
a pyrotechnic charge configured to be ignited and to combust upon ignition; and
a pressure chamber configured to receive a fluid sample containing cells and to be pressurized upon the ignition and the combustion of the pyrotechnic charge,
wherein the pyrotechnic charge is received in a pyrotechnic charge chamber separated from the pressure chamber, and
wherein the pyrotechnic charge chamber is formed in a pyrotechnic charge chamber housing that includes the pyrotechnic charge chamber and has a breaking point that ruptures upon the ignition and the combustion of the pyrotechnic charge, and the pyrotechnic charge chamber opens directly to the pressure chamber upon breaking of the breaking point.

2. The pyrotechnic cell disruption apparatus according to claim 1,
wherein the pyrotechnic charge chamber housing includes a pressure release channel at the breaking point, and
wherein the pressure release channel communicates with an interior space of the pressure chamber after the breaking point ruptures.

3. The pyrotechnic cell disruption apparatus according to claim 2, wherein the pyrotechnic charge chamber housing is disposed within the pressure chamber formed in a body of the pyrotechnic cell disruption apparatus.

4. The pyrotechnic cell disruption apparatus according to claim 3, further comprising:
a release channel disposed on an end portion of the body,
wherein the release channel connects the pressure chamber to an outside of the pyrotechnic cell disruption apparatus.

5. The pyrotechnic cell disruption apparatus according to claim 4, further comprising:
an orifice disposed in the release channel.

6. The pyrotechnic cell disruption apparatus according to claim 5,
wherein the orifice causes shear stress to act on the fluid sample when the fluid sample is distributed through the orifice.

7. The pyrotechnic cell disruption apparatus according to claim 1, further comprising:
a pressure relief that relieves a pressure from the pressure chamber after the pressure chamber is pressurized by the ignition and the combustion of the pyrotechnic charge.

8. The pyrotechnic cell disruption apparatus according to claim 1, wherein a sample container that is filled with the fluid sample is received in the pressure chamber.

9. The pyrotechnic cell disruption apparatus according to claim 8, wherein the sample container is a flexible pouch.

10. A pyrotechnic cell disruption method comprising:
receiving a fluid sample containing cells in a pressure chamber of a pyrotechnic cell disruption apparatus configured to be pressurized by a pyrotechnic charge received in a pyrotechnic charge chamber separated from the pressure chamber, wherein the pyrotechnic charge chamber is formed in a pyrotechnic charge chamber housing that includes the pyrotechnic charge chamber and has a breaking point that ruptures upon the ignition and the combustion of the pyrotechnic charge; and
pressurizing the fluid sample received in the pressure chamber by igniting and combusting the pyrotechnic charge, when the pyrotechnic charge chamber opens directly to the pressure chamber upon breaking of the breaking point.

11. The pyrotechnic cell disruption method according to claim 10
wherein the pyrotechnic charge chamber housing includes a pressure release channel at the breaking point, and
wherein the pressure release channel communicates with an interior space of the pressure chamber when the breaking point ruptures.

12. The pyrotechnic cell disruption method according to claim 11,
wherein the pyrotechnic charge chamber housing is disposed within the pressure chamber in a body of the pyrotechnic cell disruption apparatus.

13. The pyrotechnic cell disruption method according to claim 12,
wherein a release channel is disposed on an end portion of the body so that the pressurized fluid sample is pushed into the release channel to connect the pressure chamber to an outside of the pyrotechnic cell disruption apparatus.

14. The pyrotechnic cell disruption method according to claim 13,
wherein an orifice is disposed in the release channel.

15. The pyrotechnic cell disruption method according to claim 14
  wherein the orifice causes shear stress to act on the fluid sample when the fluid sample is distributed through the orifice. 5

16. The pyrotechnic cell disruption method according to claim 10, further comprising:
  relieving, via a pressure relief, a pressure from the pressure chamber after the pressure chamber is pressurized by the ignition and the combustion of the pyrotechnic 10 charge.

\* \* \* \* \*